US011471285B2

(12) United States Patent
De Peppo

(10) Patent No.: US 11,471,285 B2
(45) Date of Patent: Oct. 18, 2022

(54) TISSUE GRAFTS AND METHODS OF MAKING AND USING THE SAME

(71) Applicant: New York Stem Cell Foundation, Inc., New York, NY (US)

(72) Inventor: Giuseppe Maria De Peppo, New York, NY (US)

(73) Assignee: New York Stem Cell Foundation, Inc., New York, NY (US)

( * ) Notice: Subject to any disclaimer, the term of this patent is extended or adjusted under 35 U.S.C. 154(b) by 0 days.

(21) Appl. No.: 15/108,996

(22) PCT Filed: Dec. 29, 2014

(86) PCT No.: PCT/US2014/072579
§ 371 (c)(1),
(2) Date: Jun. 29, 2016

(87) PCT Pub. No.: WO2015/103149
PCT Pub. Date: Jul. 9, 2015

(65) Prior Publication Data
US 2016/0324642 A1 Nov. 10, 2016

Related U.S. Application Data

(60) Provisional application No. 62/087,614, filed on Dec. 4, 2014, provisional application No. 61/921,915, filed on Dec. 30, 2013.

(51) Int. Cl.
| | |
|---|---|
| *A61F 2/30* | (2006.01) |
| *C12N 5/00* | (2006.01) |
| *A61K 35/12* | (2015.01) |
| *C12M 3/00* | (2006.01) |
| *C12M 1/12* | (2006.01) |
| *C12M 1/00* | (2006.01) |
| *A61F 2/28* | (2006.01) |
| *A61L 27/38* | (2006.01) |
| *C12N 5/074* | (2010.01) |
| *A61F 2/46* | (2006.01) |

(52) U.S. Cl.
CPC ............ *A61F 2/30942* (2013.01); *A61F 2/28* (2013.01); *A61F 2/2846* (2013.01); *A61F 2/30756* (2013.01); *A61K 35/12* (2013.01); *A61L 27/3821* (2013.01); *C12M 21/08* (2013.01); *C12M 23/46* (2013.01); *C12M 25/14* (2013.01); *C12M 29/10* (2013.01); *C12N 5/0062* (2013.01); *C12N 5/0607* (2013.01); *A61F 2002/2835* (2013.01); *A61F 2002/30759* (2013.01); *A61F 2002/30762* (2013.01); *A61F 2002/30766* (2013.01); *A61F 2002/30943* (2013.01); *A61F 2002/30952* (2013.01); *A61F 2002/4648* (2013.01)

(58) Field of Classification Search
None
See application file for complete search history.

(56) References Cited

U.S. PATENT DOCUMENTS

| | | | |
|---|---|---|---|
| 5,899,939 A | 5/1999 | Boyce et al. | |
| 6,143,293 A * | 11/2000 | Weiss | A61L 27/18 424/423 |
| 6,472,202 B1 | 10/2002 | Banes | |
| 6,995,013 B2 * | 2/2006 | Connelly | A61L 27/3633 435/395 |
| 8,398,714 B2 | 3/2013 | Boiangiu et al. | |
| 8,895,046 B2 | 11/2014 | Xuenong et al. | |
| 8,926,699 B2 | 1/2015 | Burkinshaw | |
| 9,456,893 B2 | 10/2016 | Ling | |
| 2003/0100107 A1 | 5/2003 | Peschle | |
| 2004/0224380 A1 | 11/2004 | Chou et al. | |
| 2006/0253192 A1 | 11/2006 | Atala et al. | |
| 2006/0257447 A1 | 11/2006 | Hinds et al. | |
| 2008/0033548 A1 | 2/2008 | Xuenong et al. | |
| 2009/0081784 A1 * | 3/2009 | Vodyanyk | C12N 5/0662 435/372 |
| 2010/0003222 A1 * | 1/2010 | Yayon | A61K 35/12 |

(Continued)

FOREIGN PATENT DOCUMENTS

| | | |
|---|---|---|
| WO | WO 1996/040002 A1 | 12/1996 |
| WO | WO 1999/048541 A1 | 9/1999 |

(Continued)

OTHER PUBLICATIONS

CT Scan (CAT Scan, Computerized Tomography) Imaging Procedure, retrieved from the internet Dec. 7, 2018: www.medicinenet.com/cat_scan/article.htm#whatjs_a_ct_scan.*
Kohl et al., Proc Am Thorac Soc, vol. 2, pp. 470-476, 2005 (Year: 2005).*
Walter et al., RadioGraphics, Mar. 1988, vol. 8, No. 2, pp. 327-348 (Year: 1988).*
Extended European Search Report dated Jul. 7, 2017, regarding EP 14 87 7521.6.
Chen, F. et al.: "*Anchoring Dental Implant in Tissue-Engineered Bone Using Composite Scaffold A Preliminary Study in Nude Mouse Model*"; Journal of Oral and Maxillofacial Surgery, 2005, 63, 586-591.

(Continued)

*Primary Examiner* — Evelyn Y Pyla
(74) *Attorney, Agent, or Firm* — Goodwin Procter LLP

(57) ABSTRACT

In some embodiments, the present invention provides tissue grafts, such as vascularized bone grafts, and methods for preparing and using such tissue grafts. In some embodiments the tissue grafts are made using pluripotent stem cells, such as autologous pluripotent stem cells. In some embodiments, the tissue grafts are made by creating a digital model of a tissue portion to be replaced or repaired, such as a bone defect, partitioning the model into two or more model segments, and then producing tissue graft segments having a size and shape corresponding to that of the model segments. Such tissue graft segments may be assembled to form a tissue graft having a size and shape corresponding to that of the tissue portion to be replaced or repaired.

11 Claims, 5 Drawing Sheets

(56) References Cited

U.S. PATENT DOCUMENTS

| | | | |
|---|---|---|---|
| 2010/0040584 | A1 | 2/2010 | Melero-Martin et al. |
| 2010/0249931 | A1 | 9/2010 | Laurencin et al. |
| 2010/0303911 | A1 | 12/2010 | Sheardown et al. |
| 2011/0003324 | A1 | 1/2011 | Durack |
| 2011/0151400 | A1 | 6/2011 | Boiangiu |
| 2012/0035742 | A1 | 2/2012 | Vunjak-Novakovic et al. |
| 2012/0209403 | A1 | 8/2012 | Morrison et al. |
| 2012/0258488 | A1 | 10/2012 | Abilez et al. |
| 2013/0017232 | A1* | 1/2013 | Varghese ............... A61K 35/12 424/400 |
| 2013/0030547 | A1 | 1/2013 | Burkinshaw |
| 2013/0030548 | A1 | 1/2013 | Ling |
| 2013/0046392 | A1 | 2/2013 | Venu et al. |
| 2013/0274892 | A1 | 10/2013 | Lelkes et al. |
| 2013/0344114 | A1 | 12/2013 | Chang et al. |
| 2014/0030762 | A1 | 1/2014 | De Piano et al. |
| 2014/0147419 | A1 | 5/2014 | Novakovic et al. |
| 2014/0178455 | A1 | 6/2014 | Nukavarapu et al. |
| 2015/0159132 | A1 | 6/2015 | Li et al. |
| 2015/0196371 | A1 | 7/2015 | Westover |
| 2015/0289889 | A1 | 10/2015 | Altschuler et al. |

FOREIGN PATENT DOCUMENTS

| | | |
|---|---|---|
| WO | WO 2006/109137 A1 | 10/2006 |
| WO | WO-2013/010283 A2 | 1/2013 |
| WO | WO 2015/103149 A1 | 7/2015 |
| WO | WO-2015/143310 A1 | 9/2015 |

OTHER PUBLICATIONS

International Search Report dated Jun. 22, 2017, regarding PCT/US2017/025390.

Yu, X et al.: "*Bioreactor-based bone tissue engineering: The influence of dynamic flow on osteoblast phenotypic expression and matrix mineralization*" Proceedings of the National Academy of Science, vol. 101 (31); p. 11203-11208.

De Peppo et al.: "*Cultivation of Human Bone-Like Tissue from Pluripotent Stem Cell-Derived Osteogenic Progenitors in Perfusion Bioreactors*"; Methods Mol Biol., Nov. 27, 2013, vol. 1202, pp. 173-184.

Grayson at al.: "*Effects of Initial Seeding Density and Fluid Perfusion Rate on Formation of Tissue-Engineered Bone*"; Tissue Eng Part A, Jul. 11, 2008, vol. 14, pp. 1809-1820.

International Search Report dated Aug. 22, 2016, regarding PCT/US2016/025601.

International Search Report dated Feb. 16, 2016, regarding PCT/US2015/064076.

International Search Report dated Apr. 6, 2015 regarding PCT/US2014/072579.

Eldesoni, Karam et al.: "*High Calcium Bioglass Enhances Differentiation and Survival of Endothelial Progenitor Cells, Inducing Early Vascularization in Critical Size Bone Defects*"; PLOS ONE, Nov. 2013, vol. 8, No. 11, e79058.

Japanese Office Action dated Aug. 23, 2018, regarding JP 2016-543600.

Datta, N. et al.: "*Effect of bone extracellular matrix synthesized in vitro on the osteoblastic differentiation of marrow stromal cells*"; Biomaterials, Mar. 1, 2005, vol. 26, No. 9. pp. 971-977, XP027767796.

Extended European Search Report dated Oct. 31, 2019, regarding EP 17 77 6781.

Griffin, Kaitlyn S. et al.: "*Evolution of Bone Grafting: Bone Grafts and Tissue Engineering Strategies for Vascularized Bone Regeneration*", Clinic Rev Bone Miner Metab, Sep. 2, 2015, vol. 13, pp. 232-244, XP035951944.

Lovati, Arianna B et al.: "*In vivo evaluation of bone deposition in macroporous titanium implants loaded with mesenchymal stem cells and strontium-enriched hydrogel*"; J. of Biome Mater Res Part B Feb. 1, 2015, vol. 103B, pp. 448-456. XP055635131.

U.S. Appl. No. 16/088,640, filed Sep. 26, 2018, De Peppo et al.

Canadian Office Action dated Mar. 3, 2021, regarding CA Appl. No. 2,935,545.

Datta, N. et al., "Effect of Bone extracellular matrix synthesized in vitro on the osteoblastic differentiation of marrow stromal cells", Biomaterials, Elsevier Science Publishers BV., Barking, GB, vol. 26, No. 9, (Mar. 1, 2005), pp. 971-977.

European Examination Report dated Apr. 9, 2019, regarding EP 14877521.6.

European Patent Office Examination Report, EP App. No. 17776781, dated Oct. 22, 2020, 6 pages.

European Search Report dated May 6, 2020 of International Application No. PCT/US2017/62344.

Hassan et al., "A Microfluidic Biochip for Complete Blood Cell Counts at the Point-of-Care," *Singap. World Sci.* (2005), 3(4):201-213.

Jonczyk et al., "Living Cell Microarrays: An Overview of Concepts," *Microarrays* (2016), 5(11):1-29.

Notice of Reasons for Rejection, JP Appl. No. 2018-551412, dated Mar. 22, 2021, 5 pages.

Pamies et al., "Good Cell Culture Practice for Stem Cells and Stem-Cell-Derived Models," t4 Workshop Report, ALTEX Online First, Aug. 23, 2016, (4):1-44.

\* cited by examiner

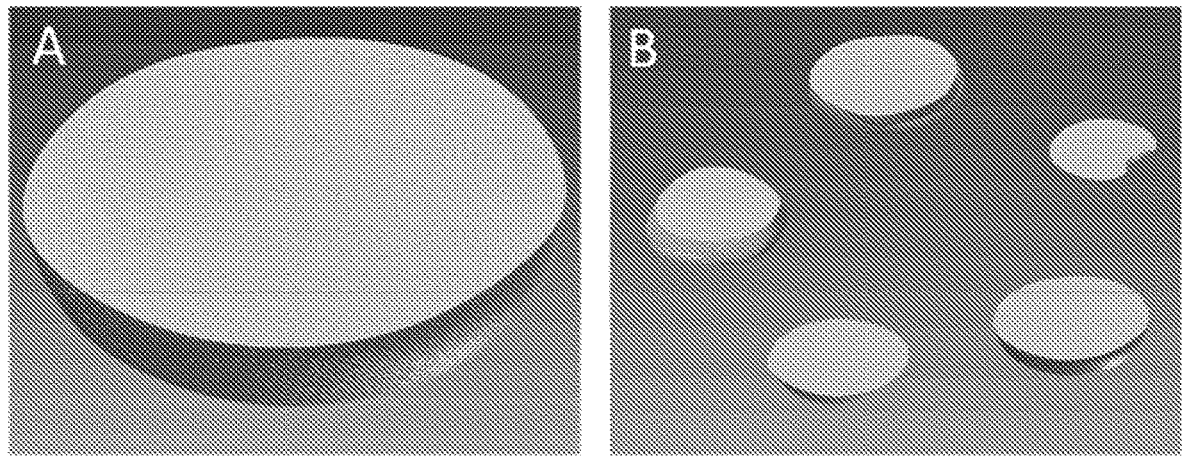
FIG. 5A-B
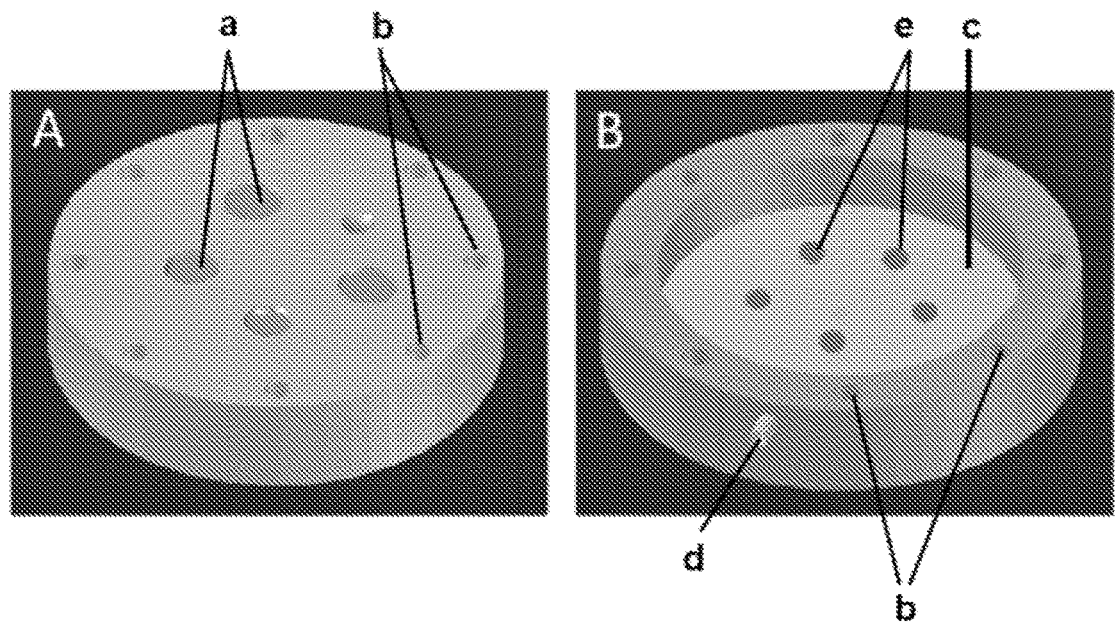
FIG. 6A-B

TISSUE GRAFTS AND METHODS OF MAKING AND USING THE SAME

CROSS-REFERENCE TO RELATED APPLICATIONS

This application is a 35 USC § 371 National Stage application of International Application No. PCT/US2014/072579 filed Dec. 29, 2014, now pending; which claims the benefit under 35 USC § 119(e) to U.S. Application Ser. No. 62/087,614 filed Dec. 4, 2014 and to U.S. Application Ser. No. 61/921,915 filed Dec. 30, 2013. The disclosure of each of the prior applications is considered part of and is incorporated by reference in the disclosure of this application.

COPYRIGHT AND INCORPORATION BY REFERENCE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

Field of the Invention

The burden of bone deficiencies resulting from trauma, birth defects and disease is massive and rapidly increasing, with a combined annual U.S. market for bone repair and regeneration therapies projected to reach 3.5 billion people by 2017. Current methods for treatment of skeletal defects are based on the insertion of implantable materials or transplantation of bone tissue. These methods have limited applicability, carry the risk of infection and/or rejection, and fail to provide outcomes of clinical relevance.

While biomimetic tissue engineering strategies have been explored for ex vivo cultivation of functional bone substitutes by interfacing osteocompetent cells to biomaterials under appropriate culture conditions in bioreactors, engineering large and geometrically complex bone grafts for extensive skeletal reconstructions remains problematic using current engineering approaches. In particular, culture of large bone grafts is problematic using common perfusion bioreactors, due to the flow resistance caused by the large size of the graft. The development of newly formed bone tissue progressively limits the medium perfusion, with negative consequences on the functionality of the perfusion system and graft viability. Thus there remains a need for new approaches and tools to facilitate the in vitro preparation of functional bone tissue and large bone grafts. Such new approaches and tools could also be used for the in vitro preparation of other types of tissue grafts, other than bone.

SUMMARY OF THE INVENTION

Some of the main aspects of the present invention are summarized below. Additional aspects of the present invention are described in the Detailed Description of the Invention, Examples, Drawings and Claims sections of this patent application. The description in each of the sections of this patent application is intended to be read in conjunction with the other sections. Furthermore, the various embodiments described in each of the sections of this patent application can be combined in various different ways, and all such combinations are intended to fall within the scope of the present invention.

In some embodiments the present invention provides novel methods, compositions and devices that can be used to overcome the obstacles associated with current methods for generating functional tissue, such as bone, in vitro. In some embodiments the methods provided by the present invention utilize three-dimensional models of a particular tissue portion (e.g. a portion of tissue to be constructed, replaced, or repaired), in order to make customized tissue culture scaffolds, customized tissue grafts, and/or customized bioreactors for producing such tissue grafts. In some such embodiments the tissue culture scaffolds, tissue grafts, and/or bioreactors are designed and produced such that they have a size and shape corresponding to that of the desired tissue portion, or a segment thereof. In some embodiments the methods of the present invention involve making tissue grafts by producing two or more tissue graft segments that can then be assembled/connected to produce the final tissue graft. Such methods may be referred to herein as segmental additive tissue engineering (SATE) methods. In addition to the various different methods provided herein, the present invention also provides certain compositions and devices, including customized tissue grafts, customized tissue culture scaffolds, customized bioreactors, customized bioreactor graft chambers, and customized bioreactor graft chamber inserts. These and other aspects of the present invention are described in more detail below and throughout the present patent specification.

In some embodiments, the present invention provides various methods for preparing tissue grafts, and segments thereof (tissue graft segments).

In one such embodiment, the present invention provides a method of preparing a tissue graft, comprising: obtaining a three-dimensional model of a tissue portion to be produced, replaced, or repaired.

In another such embodiment, the present invention provides a method of preparing a tissue graft, comprising: (a) obtaining a three-dimensional model of a tissue portion to be produced, replaced, or repaired, and (b) partitioning the three-dimensional model into two or more segments (model segments).

In another such embodiment, the present invention provides a method of preparing a tissue graft, comprising: obtaining a three-dimensional model of a tissue portion to be produced, replaced, or repaired wherein the model has been partitioned into two or segments (model segments).

In another such embodiment, the present invention provides a method of preparing a tissue graft, comprising: preparing or obtaining two or more tissue graft segments.

In another such embodiment, the present invention provides a method of preparing a tissue graft, comprising: assembling two or more tissue graft segments.

In another such embodiment, the present invention provides a method of preparing a tissue graft, comprising: (a) preparing or obtaining two or more tissue graft segments, and (b) assembling the two or more tissue graft segments to form a tissue graft.

In another such embodiment, the present invention provides a method of preparing a tissue graft, comprising: (a) obtaining a three-dimensional model of a tissue portion to be produced, replaced, or repaired, (b) partitioning the three-dimensional model into two or more model segments, (c) preparing two or more tissue graft segments, wherein each tissue graft segment has a size and shape corresponding to one of the model segments of step (b), and (d) assembling the two or more tissue graft segments to form a tissue graft.

In some embodiments the present invention provides a method of preparing a tissue graft segment (for example for use in preparing a tissue graft, as described above or elsewhere herein), wherein the method comprises: obtaining a scaffold, wherein the scaffold has a size and shape corresponding to a segment of a tissue portion to be produced, replaced, or repaired (a tissue segment) or a three dimensional model thereof (a model segment).

In some embodiments the present invention provides a method of preparing a tissue graft segment (for example for use in preparing a tissue graft, as described above or elsewhere herein), wherein the method comprises: obtaining a scaffold precursor, wherein the scaffold precursor has a size and shape corresponding to a tissue portion to be produced, replaced, or repaired (a tissue segment) or a three dimensional model thereof, and partitioning (e.g. slicing) the scaffold precursor to form two or more scaffolds, wherein the scaffold has a size and shape corresponding to a segment of a tissue portion to be produced, replaced, or repaired (a tissue segment) or a three dimensional model thereof (a model segment).

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), and (ii) applying one or more populations of cells to the scaffold.

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), (ii) applying one or more populations of cells to the scaffold, and (iii) culturing the cells on the scaffold to form a tissue graft segment.

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), (ii) applying one or more populations of cells to the scaffold, (iii) obtaining a culture vessel comprising a graft chamber configured to accommodate the scaffold, (for example having a graft chamber or graft chamber insert having an internal size and shape corresponding to the scaffold), (iv) inserting the scaffold into the graft chamber of the culture vessel, and (v) culturing the cells on the scaffold within the culture vessel to form a tissue graft segment.

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), (ii) obtaining a culture vessel comprising a graft chamber configured to accommodate the scaffold, (for example having a graft chamber or graft chamber insert having an internal size and shape corresponding to the scaffold), (iii) inserting the scaffold into the graft chamber of the culture vessel, (iv) applying one or more populations of cells to the scaffold in the graft chamber, and (v) culturing the cells on the scaffold with in the culture vessel to form a tissue graft segment.

In some embodiments, the present invention provides various methods for preparing scaffolds that may be used in the production of tissue grafts or tissue graft segments.

In one such embodiment, the present invention provides a method of preparing a scaffold precursor, comprising: obtaining a three-dimensional model of a tissue portion to be produced, replaced, or repaired, wherein the scaffold precursor has a size and shape corresponding to the tissue portion or the three dimensional model thereof.

In one such embodiment, the present invention provides a method of preparing a scaffold, comprising: obtaining a three-dimensional model of a tissue portion to be produced, replaced, or repaired, wherein the scaffold has a size and shape corresponding to a segment of the tissue portion or a segment of the three dimensional model of the tissue portion.

In another such embodiment, the present invention provides a method of preparing a scaffold, comprising: (a) obtaining a three-dimensional model of a tissue portion to be produced, replaced, or repaired, and (b) partitioning the three-dimensional model into two or more segments (model segments).

In another such embodiment, the present invention provides a method of preparing a scaffold, comprising: obtaining a three-dimensional model of a tissue portion to be produced, replaced, or repaired wherein the model has been partitioned into two or segments (model segments).

In some embodiments the present invention provides a method of preparing a scaffold, wherein the method comprises: obtaining a scaffold precursor, wherein the scaffold precursor has a size and shape corresponding to a tissue portion to be produced, replaced, or repaired, or a three dimensional model thereof, and partitioning (e.g. slicing) the scaffold precursor to form two or more scaffolds, wherein each the scaffold has a size and shape corresponding to a segment of a tissue portion to be produced, replaced, or repaired (a tissue segment) or a three dimensional model thereof (a model segment).

In some embodiments, the present invention provides various methods of preparing bioreactors, bioreactor graft chambers, or bioreactor graft chamber inserts, suitable for use in preparing the tissue grafts and/or tissue graft segments described herein.

In one such embodiment, the present invention provides a method of preparing a bioreactor, bioreactor graft chamber, or bioreactor graft chamber insert, comprising: obtaining a three-dimensional model of a tissue portion to be produced, replaced, or repaired.

In another such embodiment, the present invention provides a method of preparing a bioreactor, bioreactor graft chamber, or bioreactor graft chamber insert, comprising: (a) obtaining a three-dimensional model of a tissue portion to be produced, replaced, or repaired, and (b) partitioning the three-dimensional model into two or more segments (model segments).

In another such embodiment, the present invention provides a method of preparing a bioreactor, bioreactor graft chamber, or bioreactor graft chamber insert, comprising: obtaining a three-dimensional model of a tissue portion to be produced, replaced, or repaired wherein the model has been partitioned into two or segments (model segments).

In another such embodiment, the present invention provides a method of preparing a bioreactor, bioreactor graft chamber, or bioreactor graft chamber insert, comprising: (a) obtaining a three-dimensional model of a tissue portion to be produced, replaced, or repaired, (b) partitioning the three-dimensional model into two or more model segments, (c) preparing two or more bioreactors, bioreactor graft chambers, or bioreactor graft chamber inserts, wherein each has an internal size and shape that corresponds to the size and shape of one of the model segments of step (b).

In addition to the methods described above, numerous variations on such embodiments are envisioned and are within the scope of the present invention, including, but not limited to embodiments that combine any one or more of the methods or method steps described above, or alter the order of any of the method steps described above.

In some embodiments, the present invention provides tissue grafts, and segments thereof (tissue graft segments). For example, in some embodiments, the present invention provides tissue grafts and tissue graft segments made using any of the methods described herein.

In one embodiment the present invention provides a tissue graft comprising two or more tissue graft segments. In one embodiment the present invention provides a tissue graft comprising two or more tissue graft segments, wherein the tissue graft has a shape and size corresponding to a tissue portion to be replaced or repaired, or a three-dimensional model thereof.

In one embodiment the present invention provides a tissue graft comprising two or more tissue graft segments, wherein each tissue graft segment has a maximum thickness (i.e. at its thickest point) of from about 0.3 millimeters to about 10 millimeters.

In one embodiment the present invention provides a tissue graft comprising two or more tissue graft segments, wherein each tissue graft segment comprises tissue cells differentiated from stem cells or progenitor cells (e.g. induced pluripotent stem cells).

In one embodiment the present invention provides a tissue graft comprising two or more tissue graft segments, wherein each tissue graft segment comprises endothelial cells, such as endothelial cells differentiated from stem cells or progenitor cells (e.g. induced pluripotent stem cells).

In one embodiment the present invention provides a vascularized tissue graft comprising two or more tissue graft segments, wherein each tissue graft segment has a maximum thickness (i.e. at its thickest point) of from about 0.3 millimeters to about 10 millimeters.

In one embodiment the present invention provides a vascularized bone graft comprising two or more bone graft segments, wherein each bone graft segment has a maximum thickness (i.e. at its thickest point) of from about 0.3 millimeters to about 10 millimeters and wherein the bone graft comprises bone cells derived from stem cells or progenitor cells (e.g. induced pluripotent stem cells) and endothelial cells derived stem cells or progenitor cells (e.g. induced pluripotent stem cells).

In addition to the tissue grafts described above, numerous variations of such tissue grafts are envisioned and are within the scope of the present invention, including, but not limited to those described elsewhere in the present specification and those that combine any one or more of the elements described above or elsewhere in the application.

In some embodiments, the present invention provides bioreactors, bioreactor graft chambers, and bioreactor graft chamber inserts. For example, in some embodiments, the present invention provides bioreactors, bioreactor graft chambers, and bioreactor graft chamber inserts made using any of the methods described herein.

In one embodiment the present invention provides bioreactors, bioreactor graft chambers, and bioreactor graft chamber inserts, wherein the internal portion thereof has a size and shape corresponding to the tissue portion to be replaced or repaired, a segment of the tissue portion to be replaced or repaired, or a three-dimensional model of any thereof.

In one embodiment the present invention provides bioreactors, bioreactor graft chambers, and bioreactor graft chamber inserts, wherein the internal portion thereof is designed to accommodate a scaffold or a tissue graft segment that has a size and shape corresponding to a segment of a tissue portion to be replaced or repaired.

In one embodiment the present invention provides bioreactors, bioreactor graft chambers, and bioreactor graft chamber inserts, wherein the internal portion thereof is designed to accommodate a scaffold or a tissue graft segment, wherein each tissue graft segment has a maximum thickness (i.e. at its thickest point) of from about 0.3 millimeters to about 10 millimeters.

In addition to the bioreactors, bioreactor graft chambers, and bioreactor graft chamber inserts described above, numerous variations of such bioreactors, bioreactor graft chambers, and bioreactor graft chamber inserts are envisioned and are within the scope of the present invention, including, but not limited to, those described elsewhere in the present specification and those that combine any one or more of the elements described above or elsewhere in the application.

In some of the above embodiments, the tissue grafts or tissue graft segments are bone tissue grafts or bone tissue graft segments. In some embodiments, the tissue grafts or tissue graft segments are cartilage grafts or cartilage graft segments.

In some of the above embodiments, the tissue grafts or tissue graft segments comprise mammalian cells, such as cells from non-human primates, sheep, or rodents (such as rats or mice). In some of the above embodiments, the tissue grafts or tissue graft segments comprise human cells. In some of the above embodiments, the tissue grafts or tissue graft segments comprise one or more populations of cells derived from the same subject into which the tissue graft is to be implanted (i.e. autologous cells). In some of the above embodiments, the tissue grafts or tissue graft segments comprise one or more populations of cells derived from stem cells or progenitor cells, such as induced pluripotent stem cells.

In some of the above embodiments, the tissue grafts or tissue graft segments are vascularized. In some of the above embodiments, the tissue grafts or tissue graft segments comprise endothelial cells, such as endothelial cells derived from stem cells or progenitor cells, such as induced pluripotent stem cells.

In some of the above embodiments the three-dimensional models and/or model segments are digital models, such as digital models that provide a representation of the three-dimensional structure of a tissue portion or a segment thereof.

In some of the above embodiments the tissue graft segments have a thickness of about 20 millimeters or less, or 15 millimeters or less, or 10 millimeters or less, for example at their thickest point. For example, in some of the above embodiments the tissue graft segments have a thickness of from about 0.3 millimeters to about 10 millimeters, for example at their thickest point.

In some of the above embodiments the culture vessels are bioreactors, such as direct perfusion bioreactors. In some of the above embodiments the scaffolds or tissue graft segments are placed into bioreactors under press-fit conditions. In some of the above embodiments tissue graft segments are cultured in a bioreactor under direct perfusion and/or press-fit conditions.

In some of the above embodiments the scaffolds are generated or customized using computer assisted manufacturing, three-dimensional printing, casting, milling, laser cutting, rapid prototyping, or any combination thereof.

In some of the above embodiments the bioreactors, bioreactor graft chambers, or bioreactor graft chamber inserts are generated or customized using computer assisted manufacturing, three-dimensional printing, casting, milling, laser cutting, rapid prototyping, or any combination thereof.

In some of the above embodiments, the tissue grafts comprise two or more tissue graft segments connected using a biocompatible adhesive, stitches, sutures, staples, plates, pins, screws, or any combination thereof.

In some embodiments the methods, compositions, and devices provided by the present invention, and tissues prepared therefrom, can be useful for a variety of applications including for therapeutic purposes (such as repairing pathological or traumatic tissue defects), cosmetic purposes, or in model systems for studying diseases or developing therapeutics.

BRIEF DESCRIPTION OF THE DRAWINGS

FIG. 4A: Three-dimensional digital model of a human femur with a digital reconstruction of a bone defect to be repaired (dark gray). FIG. 4B: Partitioning of the digital model of the bone defect shown in FIG. 4A into five model segments (dark gray). The model segments can be used to drive the manufacturing of biomaterial cell scaffolds (light gray) having a size and shape that corresponds to each of the model segments.

FIGS. 5A-5B. Perspective view of exemplary cell culture scaffolds provided by the invention. FIG. 5A shows an enlarged view of a single scaffold. The scaffold can be designed and manufactured based on a digital image of a portion of tissue, as described herein. FIG. 5B shows multiple scaffolds of different shapes and sizes. Multiple scaffolds can be used, for example, to prepare complementary segments of a large bone graft, as described herein.

FIGS. 6A-6B. Perspective view of the bottom part (FIG. 6A) and top part (FIG. 6B) of an exemplary multi-chamber bioreactor provided by the invention. FIG. 6A: The bottom part comprises multiple graft chambers (a) for the collective culture of tissue segments. The graft chambers are shown in various sizes and shapes as desired to accommodate the sizes and shapes of the scaffolds and/or tissue segments. Also shown are holes (b) to facilitate fastening of the bottom part to the top part by screws. FIG. 6B: The top part comprises a fluid reservoir (c), an outlet port (d), and multiple openings (e) aligned with the graft chambers in the bottom part so as to connect the fluid reservoir to the graft chambers in the bottom part (FIG. 6A). Also shown are holes (b) to facilitate fastening of the top part to the bottom part by screws.

DETAILED DESCRIPTION OF THE INVENTION

Figure 1:
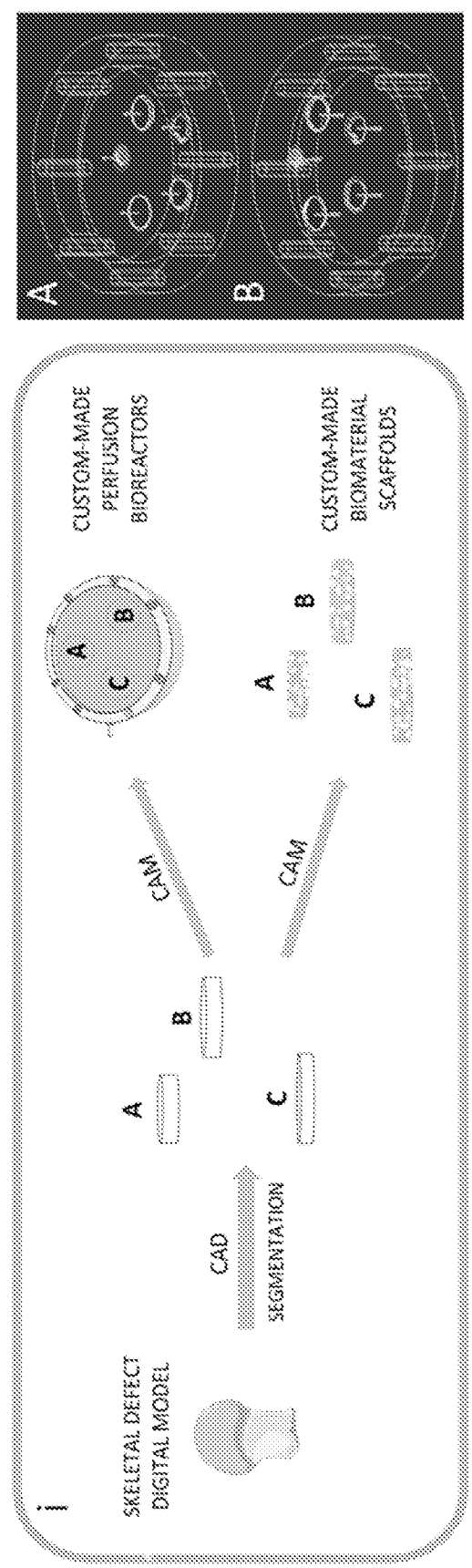
FIG. 1. (i) Digital models of skeletal defects are created, segmented (here, into three segments labeled A, B and C) and used to fabricate custom-made biomaterial scaffolds and bioreactors; (ii) Example of the top part (A) and bottom part (B) of a perfusion bioreactor created using CAD software.

In some embodiments the present invention provides, in part, tissue grafts, such as vascularized bone grafts, and methods and devices for preparing such tissue grafts, including, for example, bioreactor devices suitable for use in preparing such tissue grafts. In some embodiments the methods described herein can be used, for example, to generate a tissue graft, such as a bone graft, in vitro by segmental additive bone engineering (SABE) and/or segmental additive tissue engineering (SATE). In some embodiments the methods provided by the invention utilize digital models of portions of tissue, and/or custom-shaped tissue culture scaffolds, and/or customized bioreactors for growing segments of tissue in vitro. In some embodiments the size and shape of the scaffolds and bioreactors can be customized to correspond to the size and shape of the desired tissue graft using innovative engineering strategies, including, but not limited to, medical imaging, computer-assisted design (CAD), and/or computer-assisted manufacturing (CAM) strategies. In some embodiments functional tissue can be grown using any suitable cell capable of forming the desired tissue(s), such as a bone-forming cell (e.g., for preparation of a bone graft) or blood vessel-forming cell (e.g., for preparation of a vascularized tissue graft), or any cell capable of differentiating into a desired tissue-forming cell, such as a progenitor cell or pluripotent cell. In some embodiments such cells may be or may include a patient's own cells (i.e. autologous cells), or cells derived from a patient's own cells, for example, induced pluripotent stem cells. In some embodiments, following culture in bioreactors, multiple tissue segments may be assembled and secured together (e.g., in a "lego-like" approach) to form a tissue graft, for example a tissue graft corresponding to the dimensions and geometrical shape of a particular tissue portion, for example a tissue portion that needs to be replaced or reconstructed. Such techniques may be referred to herein as segmental additive tissue engineering (SATE), or, in the case of bone specifically, segmental additive bone engineering (SABE).

In some embodiments the tissue grafts and methods provided by the invention may be used to facilitate reproducible and/or large-scale fabrication of tissue or tissue substitutes for clinical applications, such as to repair or replace a tissue defect in a subject, such as a bone defect. As further described in the Examples and other sections of this application, some embodiments of the present invention can be used to make functional vascularized tissue grafts, such as functional vascularized bone grafts. Production of large, geometrically defined tissue grafts, for example using cells such as induced pluripotent stem cells, is a novel, innovative strategy at the interface between stem cell biology and medical engineering that can be used for a variety of purposes including but not limited to clinical applications, modeling of pathologies and drug screening.

Some of the main embodiments of the present invention are described in the above Summary of the Invention section of this application, as well as in the Examples, Figures and Claims. This Detailed Description of the Invention section provides additional description relating to the compositions and methods of the present invention, and is intended to be read in conjunction with all other sections of the present patent application, including the Summary of the Invention, Examples, Figures and Claims sections of the present application.

Abbreviations & Definitions

The abbreviation "CAD" refers to computer-aided design.

The abbreviation "CAM" refers to computer-aided manufacture.

The abbreviation "CNC" refers to computer-numerical-control.

As used herein, the terms "cell/scaffold" and "scaffold/cell" and "cell/scaffold construct" and "cell/scaffold complex" and "scaffold/cell construct" and "scaffold/cell complex" are used interchangeably to refer to a scaffold to which cells have been applied.

As used herein, the terms "about" and "approximately," when used in relation to numerical values, mean within + or −20% of the stated value.

Additional definitions and abbreviations are provided elsewhere in this patent specification or are well known in the art.

Size and Shape Variations

As used herein, the terms "corresponding to" and "correspond to," when used in relation to any aspect of the present invention where size and shape matching of two or more elements is contemplated, can mean any of the size and shape variations described in this section. Such variations described in this section can apply equally to all aspects of the present invention where size and shape matching of two or more elements is contemplated. Such elements include, tissue portions, tissue models, tissue grafts, model segments, tissue segments, bioreactors, bioreactor chambers (e.g. bioreactor graft chambers) and inserts (e.g. bioreactor graft chamber inserts), scaffolds, scaffold precursors, cell/scaffold constructs, and any other element of the invention as described in the present application.

The illustrative embodiments in this section describe size and shape variations between two elements of the invention—a first element and a second element. However the present invention contemplates that any desired number of elements, such as three, four, five or more, may have corresponding sizes and shapes as described herein. Numerous combinations of elements are envisioned and are within the scope of the present invention, including, but not limited to those described elsewhere in the present specification and those that combine any one or more of the elements described above or elsewhere in the application. The variations described in this section apply equally to any such combinations where elements may be matched by size and shape.

In some embodiments where a first element has a size and shape corresponding to a second element, the first element has the same, or about the same, or approximately the same size and shape as the second element. In some embodiments where a first element has a size and shape corresponding to a second element, the first element has a similar or complementary size and shape as the second element.

In some embodiments where a first element has a size and shape corresponding to the size and shape of a second element, the size and shape of the first element varies by plus or minus 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% of the size and shape of the second element.

For example, in some embodiments the present invention provides a three-dimensional model having a size and shape corresponding to a particular tissue portion (e.g. a portion of tissue to be constructed, replaced, or repaired). In some embodiments the present invention provides a three-dimensional model segment having a size and shape corresponding to a cell scaffold, a bioreactor, a graft chamber, a graft chamber insert, and/or a tissue segment. In some embodiments the present invention provides a cell scaffold or cell scaffold precursor having a size and shape corresponding to a tissue portion model, a model segment, a bioreactor, a graft chamber, a graft chamber insert, a tissue segment, and/or a tissue graft. In some embodiments the present invention provides a bioreactor having a size and shape corresponding to a tissue portion model, a model segment, a scaffold, a graft chamber, a graft chamber insert, a tissue segment, and/or a tissue graft. In some embodiments the present invention provides a bioreactor graft chamber or a bioreactor graft chamber insert having a shape and size corresponding to tissue portion model, a model segment, a tissue segment, and/or a tissue graft. In some embodiments the present invention provides a tissue segment having a size and shape corresponding to a model segment, a bioreactor, a scaffold, a graft chamber, and/or a graft chamber insert. In some embodiments the present invention provides a tissue graft having a size and shape corresponding to a particular tissue portion and/or a three-dimensional model of a particular tissue portion.

Acceptable variations in size and shape can also be determined based on the desired function of the two or more elements to be matched by size and shape. In some embodiments where a first element has a size and shape corresponding to the size and shape of a second element, the first and second elements can have any suitable size and shape suitable that allows one or both elements to perform a desired function and/or have a desired property. For example, in some such embodiments a tissue graft has a size and shape corresponding to a portion of tissue to be repaired provided that the tissue graft is capable of suitably repairing the tissue portion. In some such embodiments a cell scaffold has a size and shape corresponding to a graft chamber or graft chamber insert provided that the cell scaffold fits into the graft chamber or graft chamber insert under press fit conditions.

In addition, a person having ordinary skill in the art will appreciate that other acceptable variations in size and shape can be determined and that such variations are intended fall within the scope of the present invention.

Three-Dimensional Models

Figure 4A:
FIGS. 4A-4B.
Figure 4B:
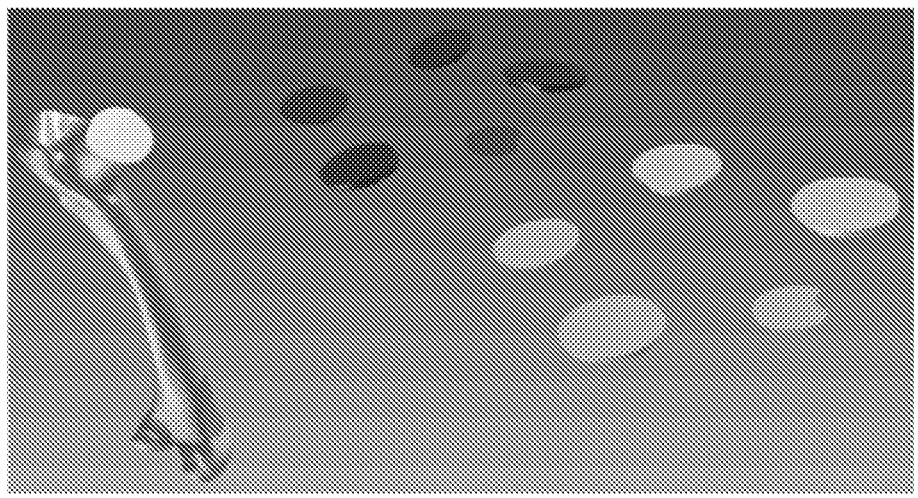

In some embodiments of the present invention, three-dimensional models of a particular tissue or tissue portion may be generated and/or used, for example to serve as a template for the production of a tissue graft or tissue graft segment, and/or to serve as a template for the production of a scaffold material to be used in the manufacture of such a tissue graft or tissue graft segment, and/or to serve as a template for the production of a bioreactor, bioreactor chamber, or bioreactor chamber insert that could be used in the production of a tissue graft or tissue graft segment. See, for example, FIGS. 4A-4B and FIG. 6. In some embodiments such three-dimensional models are digital models, such as digital models that represent the three-dimensional shape and size of a tissue portion of interest. For example, three-dimensional models or images, such as digital models or images of structures inside the body, can be generated by any suitable method known in the art, including, for example, computed tomography (CT) (including small-scale CT such as micro-CT) which uses x-rays to make detailed pictures of internal body structures and organs. In some embodiments medical imaging technologies can be used to generate a digital model of a desired tissue portion, for example a tissue portion comprising a defect, such as a skeletal defect, and that digital model can then be used to facilitate the manufacture of a tissue graft, and/or one or more tissue graft segments—for example by enabling the production of a scaffold material and/or bioreactor that is custom designed to be used in the manufacture of the desired tissue graft or tissue graft segment. A model of a tissue portion will preferably be anatomically accurate, having dimensions, geometry, size and shape that correspond to the physical tissue portion and/or the desired tissue graft. In some embodiments, the portion of tissue may comprise a defect, such as a traumatic or pathological defect. In some embodiments, such defect can be repaired a using a tissue graft prepared according to the present invention. Digital models of tissue portions can be created using any suitable computer-aided design (CAD) software, such as Autocad, Solidworks, ProE, or Creo. In some embodiments a digital model of a tissue portion can be edited and segmented/partitioned into two or more smaller sub-parts or segments (which may be referred to as "model segments" or "model portions"), for example representing tissue graft segments that can be prepared according to the present invention, and/or representing scaffold materials or bioreactor chambers that can be used for the preparation of such tissue graft segments. The thickness of the model segments can be selected such that a tissue graft segment having the same thickness could be effectively perfused in a bioreactor. Thus, in some embodiments, a model segment, and/or a corresponding tissue graft segment (e.g. a bone graft segment), has a thickness or a maximum thickness of about one centimeter or less. In some embodiments, the model segment and/or the corresponding tissue graft segment has a thickness or a maximum thickness of about 0.3 millimeters to about 10 millimeters, or about 0.3 millimeters to about 5 millimeters, or about 0.3 millimeters to about 1 millimeter. In some embodiments, the model segment and/or the corresponding tissue graft segment has a thickness of about 0.3, about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10 millimeters.

The models, such as digital models, described herein can be used to design and manufacture customized bioreactors and/or customized scaffolds to grow physical tissue graft segments having a size and shape corresponding to the complementary models. In the case of digital models, the models or model segments can be created using, or converted into, any suitable file formats, for example, IGES or SLT formats, and can be created using, or imported into, any suitable computer-aided manufacturing (CAM) software, for example, SprutCAM. Manufacture of custom bioreactors and scaffolds is further described herein.

Digital models of tissues, and segments thereof, provided by the invention can be generated, edited and otherwise manipulated as described herein. In addition, a person having ordinary skill in the art will appreciate that any other suitable methods may be used to generate, edit or otherwise manipulate digital models of tissues or segments thereof as described herein.

Cell Scaffolds

In some embodiments, the present invention provides scaffolds suitable for use in the preparation of tissue grafts and/or tissue graft segments, for example as described herein. Scaffolds can be made of any suitable material having appropriate pore sizes, porosity and/or mechanical properties for the intended use. Such suitable materials will typically be non-toxic, biocompatible and/or biodegradable, and capable of infiltration by cells of the desired tissue graft type, for example bone-forming cells in the case of bone tissue grafts. Non-limiting examples of such materials include de-cellularized tissue (such as de-cellularized bone), materials that comprise or one or more extracellular matrix ("ECM") components such as collagen, laminin, and/or fibrin, and natural or synthetic polymers or composites (such as ceramic/polymer composite materials). In some embodiments the scaffold material may be capable of being absorbed by cells (e.g., resorbable materials), while in other embodiments non-resorbable scaffold materials may be used. In some embodiments, the scaffold may comprise, consist of, or consist essentially of, any of the above-listed materials, or any combination thereof.

In some embodiments, the dimensions and geometry of a scaffold correspond to that of a three-dimensional model, such as a digital model, of a tissue portion or tissue segment, and/or correspond to that of the desired tissue graft of tissue graft segment, as described above. In some embodiments the dimensions and geometry of a scaffold can be designed or selected based on such a model in order to facilitate culturing of cells, e.g., tissue-forming cells or other cells as described herein, on the scaffold within a bioreactor, as further described below, for example in order to produce a tissue graft or tissue graft segment having a size and shape corresponding to a model or model segment. In some embodiments, scaffolds may be designed to fit into a bioreactor chamber of suitable size and shape to allow direct perfusion of the scaffold and the cells therein (e.g. during the process of producing the tissue graft and/or tissue graft segment) under press-fit conditions. FIGS. 5A-5B show illustrative scaffolds as provided herein.

In some embodiments, the scaffold is generated or customized using computer-assisted manufacturing. For example, a tissue model segment file can be used with, CAM software to drive the fabrication of geometrically defined scaffolds using any suitable method known in the art, or a combination thereof, for example, computer-controlled milling methods, rapid prototyping methods, laser cutting methods, three-dimensional printing, and/or casting technologies. In some embodiments, manufacturing of the scaffold comprises using rapid prototyping, a milling machine, casting technologies, laser cutting, and/or three-dimensional printing, or any combination thereof. In some embodiments, manufacturing of the scaffold comprises using computer-numerical-control, such as when the manufacturing comprises laser cutting or using a milling machine. For example, digital models, such as those generated using CAD software as described above, can be processed to generate the appropriate codes (such as "G-Codes") to drive a computer-numerical-control (CNC) milling machine (for example, Tormach, Bridgeport) and to select appropriate machining tool bits and program machining paths to cut the scaffold material into the desired shapes and sizes (e.g., corresponding to that of a digital models of a tissue segment).

While scaffolds provided by the invention can be designed and manufactured as described herein, a person having ordinary skill in the art will appreciate that a variety of other methods of designing and manufacturing may be used to generate scaffolds according to the present invention.

Bioreactors

In some embodiments, the present invention provides culture vessels, such as bioreactors, suitable for use in the preparation of tissue grafts and tissue graft segments, for example as described herein. In some embodiments, the bioreactors are perfusion bioreactors, for example, direct perfusion bioreactors. Perfusion bioreactors for tissue engineering applications are culture systems that typically comprise several elements, including, but not limited to one or more chambers where cell/scaffold constructs are placed (referred to herein as a "graft chamber"), a culture medium reservoir, a tubing circuit, and a pump enabling mass transport of nutrients and oxygen. Perfusion bioreactors may be broadly classified into indirect or direct systems, depending on whether the culture medium is perfused around or through the cell/scaffold constructs. For a review of bioreactors, see Sladkova and de Peppo (2014), "Bioreactor systems for human bone tissue engineering," *Processes* 2(2) 494-525, the contents of which are hereby incorporated by reference With direct perfusion bioreactors, cell/scaffold constructs are placed in a suitable graft chamber in a press-fit fashion so that the culture medium is forced to pass through the cell/scaffold construct, rather than around the cell/scaffold construct. Direct perfusion bioreactors have been used to engineer bone substitutes using a combination of different human osteocompetent cells and biomaterial scaffolds. Furthermore, in the case of bone engineering, studies demonstrate that direct perfusion of different combinations of cell/scaffold constructs can support cell survival and proliferation, and formation of mature bone-like tissue in vitro (for review, see Sladkova and de Peppo (2014), as cited above).

In some embodiments, the present invention provides certain novel bioreactors, such as novel direct perfusion bioreactors, and methods for designing and making such novel bioreactors. For example, in some embodiments models, such as digital models, of tissue portions or segments thereof, as described above, can be used to design and manufacture bioreactors that can accommodate one or more cell/scaffold constructs in a press-fit fashion under direct perfusion conditions. In some such embodiments CAD files of a tissue segment can be used to fabricate bioreactors, or graft chambers of bioreactors, or inserts for graft chambers of bioreactors, such that the bioreactor graft chamber has a size and geometry that is custom-designed to correspond to that of the tissue graft or tissue graft segment to be produced therein, and such that the scaffold and/or tissue graft/graft segment fits snugly within the bioreactor graft chamber in a press-fit configuration. Such bioreactors, or the graft chambers or graft chamber inserts thereof, can be made out of any suitable material. Materials that are suitable for the manufacture of bioreactors, or inserts thereof, are known in the art and any such materials can be used. For example, in some embodiments bioreactors, or chambers or inserts thereof, may be made of an inert metal, such as stainless steel, or made of biocompatible plastic, or any other suitable material known in the art.

In some embodiments, a bioreactor, bioreactor graft chamber, or bioreactor graft chamber insert is generated or customized using computer-assisted manufacturing. For example, in some such embodiments tissue segment files can be imported into CAM software to drive the fabrication or customization of bioreactors, bioreactor graft chambers, or bioreactor graft chamber inserts capable of accommodating geometrically defined scaffolds and/or tissue grafts or tissue graft segments using any suitable method known in the art, or a combination thereof. In some such embodiments, manufacturing or customization of the bioreactor may comprise using a rapid prototyping method, using a milling machine, using casting technologies, using laser cutting, and/or using three-dimensional printing. In some embodiments, manufacturing or customization of a bioreactor, bioreactor graft chamber, or bioreactor graft chamber insert may comprise using computer-numerical-control methods, such as when the manufacturing or customization process involves laser cutting or using a milling machine. For example, in some embodiments digital models generated using CAD software, for example, as described above may be processed to generate the appropriate G-Codes to drive a computer-numerical-control (CNC) milling machine (for example, Tormach, Bridgeport) and/or to select appropriate machining tool bits and/or program machining paths to cut the bioreactor, bioreactor graft chamber, or bioreactor graft chamber insert material into the desired shapes (e.g., complementary to the digital models of the tissue segments). In addition, digital drawing and simulation software can be used to optimize the design of bioreactors, bioreactor graft chambers, or bioreactor graft chamber inserts, and to drive the controlled manufacturing or customization thereof. In some embodiments bioreactors, bioreactor graft chambers, or bioreactor graft chamber inserts, can be designed based on digital models of tissues or tissue segments to facilitate culturing of cells, e.g., tissue-forming cells or other cells as described herein or known in the art, on scaffolds in order to produce a tissue graft or tissue graft segment having a size and shape corresponding to the complementary digital model of the tissue or tissue segment.

In some embodiments a bioreactor according to the present invention may comprise a top element and a bottom element, wherein the top element and the bottom element are secured together, for example by screws or latches, to form one or more internal chambers, including but not limited to a graft chamber. In one embodiment, the top element comprises a reservoir for culture medium, a fluid outlet port and one or more fluid channels. In one embodiment, the bottom element comprises a fluid inlet port and one or more fluid channels.

In some embodiments, the bioreactors of the invention may comprise a graft chamber that is designed or customized in order to accommodate a scaffold, tissue graft, or tissue graft segment of the desired shape and size. In one embodiment this may be achieved by designing or customizing the bioreactor itself such that it has a graft chamber having the desired shape and size. In another embodiment this may be achieved using a graft chamber insert that, when placed inside a bioreactor, produces a graft chamber that has the desired shape and size. In one embodiment, a bioreactor according to the present invention comprises a graft chamber of a size sufficient to accommodate a scaffold, tissue graft, or tissue graft segment having a thickness of about 0.3 millimeters to about 10 millimeters. In some embodiments, the scaffold and/or tissue graft segment may be positioned in the graft chamber using a graft chamber insert, which may also be referred to herein as a "frame." As described above, frames or graft chamber inserts may be used to customize the size and shape of a graft chamber and position a scaffold and/or tissue graft segment in the graft chamber, as desired, for example in order to allow culture the tissue graft segment under direct perfusion, press-fit conditions to maximize the flow of fluid through the scaffold and/or tissue graft segment, and minimize the flow of fluid around the scaffold and/or tissue graft segment. In some embodiments the graft chamber may have a generic shape or size, but one or more frames or graft chamber inserts may be used to customize the size and shape (e.g., the internal size and shape) of the graft chamber, as desired, to accommodate the scaffold and/or tissue graft segment. Frames or graft chamber inserts may be made of any suitable material. For example, in some embodiments the frame and/or graft chamber insert may comprise, consist essentially of, or consist of, a biocompatible, non-toxic, moldable plastic, such as silicone or a silicone-like material. In some such embodiments, the frame and/or graft chamber insert may comprise polydimethylsiloxane (PDMS). Frames or graft chamber inserts may be designed and manufactured by any suitable method, including, but not limited to, the methods described herein.

In some embodiments, the bioreactors of the present invention may comprise more than one graft chamber to facilitate the collective culture of multiple tissue graft segments (see FIGS. 6A-6B). For example, in one embodiment a bioreactor according to the present invention may be configured to accommodate the culture of one, two, three, four, five or more tissue graft segments, as desired.

In some embodiments bioreactors, bioreactor graft chambers, and graft chamber frames or inserts, as provided by the present invention, can be designed and manufactured as described herein, for example using computer-aided design (CAD) and computer-aided manufacture (CAM) methods. However, a person having ordinary skill in the art will appreciate that a variety of other methods of may be used to generate and customize bioreactors, bioreactor graft chambers, and bioreactor graft chamber frames or inserts according to the present invention.

Cells

Any suitable or desired type of cell or cells may be used in the preparation of tissue grafts or tissue graft segments in accordance with the present invention, as described herein. Typically the selected cell(s) will be capable of forming the desired tissue graft (for example, for a vascularized bone graft, mesenchymal progenitor cells and endothelial progenitor cells or any other cell types suitable for or capable of forming bone and blood vessels, as further described herein), or any cell(s) capable of differentiating into the desired tissue-forming cell(s) (for example, a pluripotent cell). Non-limiting examples of cells that may be used include pluripotent cells, stem cells, embryonic stem cells, induced pluripotent stem cells, progenitor cells, tissue-forming cells, or differentiated cells.

The cells used may be obtained from any suitable source. In some embodiments, the cells may be human cells. In some embodiments, the cells may be mammalian cells, including, but not limited to, cells from a non-human primate, sheep, or rodent (such as a rat or mouse). For example, cells may be obtained from tissue banks, cell banks or human subjects. In some embodiments, the cells are autologous cells, for example, cells obtained from the subject into which the prepared tissue graft will be subsequently transplanted, or the cells may be derived from such autologous cells. In some embodiments, the cells may be obtained from a "matched" donor, or the cells may be derived from cells obtained from a "matched" donor. For cell and tissue transplants, donor and recipient cells can be matched by methods well known in the art. For example, human leukocyte antigen (HLA) typing is widely used to match a tissue or cell donor with a recipient to reduce the risk of transplant rejection. HLA is a protein marker found on most cells in the body, and is used by the immune system to detect cells that belong in the body and cells that do not. HLA matching increases the likelihood of a successful transplant because the recipient is less likely to identify the transplant as foreign. Thus, in some embodiments of the present invention, the cells used are HLA-matched cells or cells derived from HLA-matched cells, for example, cells obtained from a donor subject that has been HLA-matched to the recipient subject who will receive the tissue graft. In some embodiments the cells used may be cells that have been modified to avoid recognition by the recipient's immune system (e.g. universal cells). In some such embodiments the cells are genetically-modified universal cells. For example, in some embodiments the universal cells may be MHC universal cells, such as major histocompatibility complex (MHC) class I-silenced cells (see for example Figueiredo C. et al. "MHC universal cells survive in an allogeneic environment after incompatible transplantation" Biomed Res Int 2013: 796046. Doi: 10.1155/2013/796046). Human MHC proteins are referred to as HLA because they were first discovered in leukocytes. Universal cells have the potential to be used in any recipient, thus circumventing the need for matched cells.

In some embodiments, the cells used in making the tissue grafts of the present invention are, or include, pluripotent stem cells, such as induced pluripotent stem cells (iPSCs). In some such embodiments, the pluripotent stem cells may be generated from cells obtained from the subject (i.e. autologous cells) that will receive the tissue graft. In other such embodiments, the pluripotent stem cells may be generated from cells obtained from a different individual—i.e. not the subject that will receive the tissue graft (i.e. allogeneic cells). In some such embodiments, the pluripotent stem cells may be generated from cells obtained from a different individual—i.e. not the subject that will receive the tissue graft—but where that different individual is a "matched" donor—for example as described above. In some embodiments, the cells used are differentiated cells, such as bone cells. In some embodiments, the differentiated cells are derived from pluripotent stem cells, such as induced pluripotent stem cells. In some embodiments, the differentiated cells are derived by trans-differentiation of differentiated somatic cells, or by trans-differentiation of pluripotent cells (such as pluripotent stem cells or induced pluripotent stem cells), for example induced pluripotent stem cells generated from somatic cells.

A pluripotent stem cell is a cell that can (a) self-renew and (b) differentiate to produce cells of all three germ layers (i.e. ectoderm, mesoderm, and endoderm). The term "induced pluripotent stem cell" encompasses pluripotent stem cells, that, like embryonic stem cells (ESC), can be cultured over a long period of time while maintaining the ability to differentiate into cells of all three germ layers, but that, unlike ES cells (which are derived from the inner cell mass of blastocysts), are derived from somatic cells, that is, cells that had a narrower, more defined potential and that in the absence of experimental manipulation could not give rise to cells of all three germ layers. iPSCs generally have an hESC-like morphology, growing as flat colonies with large nucleo-cytoplasmic ratios, defined borders and prominent nuclei. In addition, iPSCs generally express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, iPSCs, like other pluripotent stem cells, are generally capable of forming teratomas. In addition, they are generally capable of forming or contributing to ectoderm, mesoderm, or endoderm tissues in a living organism.

Illustrative iPSCs include cells into which the genes Oct-4, Sox-2, c-Myc, and Klf have been transduced, as described by Takahashi and Yamanaka (Cell 126(4):663-76 (2006), the contents of which are hereby incorporated by reference in their entirety). Other exemplary iPSCs are cells into which OCT4, SOX2, NANOG, and LIN28 have been transduced (Yu, et al., Science 318:1917-1920 (2007), the contents of which are hereby incorporated by reference in their entirety). One of skill in the art would know that various different cocktails of reprogramming factors can be used to produce iPSCs, such as factors selected from the group consisting of OCT4, SOX2, KLF4, MYC, Nanog, and Lin28. The methods described herein for producing iPSCs are illustrative only and are not intended to be limiting. Rather any suitable methods or cocktails of reprogramming factors known in the art can be used. In embodiments where reprogramming factors are used, such factors can be delivered using any suitable means known in the art. For example, in some embodiments any suitable vector, such as a Sendai virus vector, may be used. In some embodiments reprogramming factors may be delivered using modified RNA methods and systems. A variety of different methods and systems are known in the art for delivery of reprogramming factors and any such method or system can be used.

Any culture medium suitable for culture of cells, such as pluripotent stem cells, may be used in accordance with the present invention, and several such media are known in the art. For example, a culture medium for culture of pluripotent stem cells may comprise Knockout DMEM, 20% Knockout Serum Replacement, nonessential amino acids, 2.5% FBS, Glutamax, beta-mercaptoethanol, 10 ng/microliter bFGF, and antibiotic. The employed medium may also be a variation of this medium, for example without the 2.5% FBS, or with a higher or lower % of knockout serum replacement, or without antibiotic. The employed medium may also be any other suitable medium that supports the growth of human pluripotent stem cells in undifferentiated conditions, such as mTeSR (available from STEMCELL Technologies), or Nutristem (available from Stemgent), or ES medium, or any other suitable medium known in the art. Other exemplary methods for generating/obtaining pluripotent stem cells from a population of cells obtained from a subject are provided in the Examples of the present application.

In some embodiments, pluripotent stem cells are differentiated into a desired cell type, for example, a bone-forming cell or a blood vessel-forming cell, or any other desired cell type. Differentiated cells provided by the invention can be derived by various methods known in the art using, for example, adult stem cells, embryonic stem cells (ESCs), epiblast stem cells (EpiSCs), and/or induced pluripotent stem cells (iPSCs; somatic cells that have been reprogrammed to a pluripotent state). Methods are known in the art for directed differentiation or spontaneous differentiation of pluripotent stem cells, for example by use of various differentiation factors. Differentiation of pluripotent stem cells may be monitored by a variety of methods known in the art. Changes in a parameter between a stem cell and a differentiation factor-treated cell may indicate that the treated cell has differentiated. Microscopy may be used to directly monitor morphology of the cells during differentiation.

In each of the embodiments of the invention, any suitable or desired types of cells can be used to produce the tissue grafts and tissue graft segments described herein, including, but not limited to, pluripotent stem cells or progenitor cells or differentiated cells. In some embodiments, the pluripotent stem cells may be induced pluripotent stem cells. In embodiments where induced pluripotent stem cells are used, such cells may be derived from differentiated somatic cells obtained from a subject, for example by contacting such differentiated somatic cells with one or more reprogramming factors. In some embodiments, pluripotent cells may have been induced toward a desired lineage, for example, mesenchymal lineage or endothelial lineage. In some embodiments, the differentiated cells can be any suitable type of differentiated cells. In some embodiments, the differentiated cells may be derived from pluripotent stem cells (such as induced pluripotent stem cells), for example by contacting such pluripotent cells with one or more differentiation factors. In some embodiments, the differentiated cells may be derived by trans-differentiation of another differentiated cell type, for example by contacting the cells with one or more reprogramming factors. In the various embodiments of the present invention involving differentiated cells, such differentiated cells may be any desired differentiated cell type, including, but not limited to, bone cells and blood vessel cells.

Cell/Scaffold Constructs

Any suitable or desired type of cell, such as the cell types described herein, can be applied to or seeded onto a scaffold to prepare tissue graft or tissue graft segment according to the present invention.

In some embodiments, cells may be in a differentiated state prior to being applied to a scaffold. For example, in some embodiments differentiated cells may be obtained and used directly. Similarly, in some embodiments non-differentiated cells may be cultured according to any suitable method known in the art, such as in a culture dish or multi-well plate or in suspension, for a suitable period or length of time, for example, until desired levels of cell growth or differentiation or other parameters are achieved, then the differentiated cells may be transferred to the scaffold and subsequently the cell/scaffold construct is inserted into a bioreactor to facilitate development of a tissue graft or tissue graft segment. In some embodiments, non-differentiated cells (for example, stem cells (such as iPSCs) or progenitor cells) may be applied to the scaffold. In such embodiments, the non-differentiated cells may undergo differentiation while being cultured on the scaffold.

In some embodiments, two or more different cell populations may be seeded onto a scaffold to prepare a cell/scaffold construct. For example, in some embodiments both bone-forming cells and blood vessel-forming cells may be seeded onto a scaffold and co-cultured for the preparation of a vascularized bone graft (see FIG. 7). In some embodiments, the two or more populations of cells are co-cultured on the scaffold for a suitable period of time, for example, until desired levels of growth or differentiation or other parameters are achieved, before the cell/scaffold construct is inserted into the bioreactor. Populations of cells may comprise, consist essentially of, or consist of, any desired type of cell in any stage of growth or differentiation, and any combinations thereof. For example, in some embodiments, each cell population may comprise cells capable of forming a different tissue, for example for the preparation of a vascularized bone graft, a first population containing cells capable of forming bone, such as mesenchymal progenitor cells, and a second population containing cells capable of forming blood vessels, such as endothelial progenitor cells. In some embodiments, each population of cells may comprise cells capable of forming the same tissue (e.g., bone) but each population of cells may be at different stages of differentiation (e.g., mesenchymal stem cells and bone marrow stromal cells). Populations of cells to be co-cultured may be applied to a scaffold at the same time or at different times, as desired. Where two or more populations of cells are applied at different times, the sequence or order of co-culture (e.g., which population is applied to the scaffold first, which population is applied to the scaffold second, etc.) may be selected as desired, for example depending on the cell types being used, the state or growth or differentiation of the populations of cells, or any other parameters, as desired. Where two or more populations of cells are to be applied to the scaffold, they can be applied at any suitable cell ratio, as desired. For example, in some embodiments two different populations of cells may be seeded at a ratio of about 1:1, or any ratio from about 2:8 to about 8:2. In some embodiments, the cell populations may be seeded at a ratio of about 2:8, about 3:7, about 4:6, about 5:5, about 6:4, about 7:3, or about 8:2.

A cell/scaffold construct may be transferred to a bioreactor at any suitable point, for example, immediately after seeding with cells, following a certain period of cell culture following seeding, after the seeded cells have reached a desired state of differentiation or any other desired state, as desired. In some embodiments the cell/scaffold construct is inserted into a bioreactor and cultured under press fit conditions to allow formation of a tissue graft or tissue graft segment. Tissue/graft development can be assessed using any suitable qualitative or quantitative methods known in the art, including but not limited to histological and immunohistochemical examination, biochemical assays, high-resolution characterization techniques (e.g., SEM, FIB-TEM, Tof-SIMS), imaging procedures (e.g., CT or microCT) and mechanical testing (e.g., Young's modulus, tensile and compressive strength).

A person having ordinary skill in the art will recognize that countless variations and combinations of cells and culture methods will fall within the scope of the present invention. For example, cell culture methods, including cell seeding ratios, concentration of differentiation factors and sequence of co-culture, will typically be determined according to the desired cell type being used or the tissue graft being prepared.

Tissue Grafts, and Assembly and Use Thereof

In some embodiments, the present invention provides tissue grafts, such as bone grafts, that are assembled from multiple tissue graft segments. The present invention also provides methods of making such tissue grafts. Such methods may be referred to as segmental additive tissue engineering (SATE) methods. In the case of bone grafts in particular, such methods may be referred to as segmental additive bone engineering (SABE) methods. At any suitable point, for example when a tissue graft segment having the desired properties has been produced, tissue graft segments can be removed from the bioreactor in which they are produced and multiple tissue graft segments can be assembled together to form a tissue graft having the desired size and shape, for example a size and shape corresponding to the tissue portion to be replaced.

Assembled tissue graft segments can be secured or attached together by any suitable means or method capable of maintaining the intended assembly of the segments. For example typically, such securing means or methods will be non-toxic, biocompatible and/or resorbable (e.g., capable of being absorbed by the body), for example, where the assembled tissue graft will be transplanted into a subject. For example, in some embodiments, the tissue graft segments may be secured to each other using an adhesive, stitches or sutures, staples, plates, pins and holes, screws, bolts, or the like, as desired. In some embodiments, the means used to secure the tissue segments together are biocompatible or resorbable or both.

In some embodiments, where an adhesive is used to secure the graft segments to each other, the adhesive may be a biocompatible glue, for example, a biocompatible polymer glue such as NovoSorb (PolyNovo Biomaterials, Melbourne) or any gel, liquid, rubber-like substance, or other biocompatible adhesive material capable of securing together two or more tissue graft segments. For example, in the case of bone grafts, exemplary bone glues that can be used to secure bone graft segments to each other include, but are not limited to, polymer-based or polymeric bone glues such as polyurethane-based and polymethylmethacrylate-based bone glues. In some embodiments, the adhesive may be a tape, for example, a surgical tape. In some embodiments, tissue graft segments may be secured to each other using one or more plates, pins, screws, bolts, staples, stitches, sutures, or the like, for example made of plastic, metal (for example, titanium) or any other suitable material. In some embodiments such pins, screws, bolts, staples, stitches, sutures, or the like may be manufactured using 3D printing or any other suitable method known in the art.

In some embodiments, various different means and/or methods to secure the assembled tissue graft segments together may be used in combination, for example, to reinforce the connection between the assembled tissue graft segments and/or to attach or anchor or secure the tissue graft to the host tissues, such as where a tissue graft is transplanted into a subject (see FIG. 8). For example, in some embodiments engineered bone graft segments as described herein can be assembled together using both a biocompatible bone glue and metallic or resorbable pins.

Following assembly and securing together of the tissue graft segments, the resulting tissue graft can be transplanted into a subject, where it may also be anchored to the subject's tissues (such as surrounding bone in the case of a bone graft). In some embodiments, the methods and compositions provided by the present invention may be used to engineer tissue grafts for clinical applications, including therapeutic and/or cosmetic applications. Non-limiting examples of such applications include repair or replacement of a tissue defect or damage or tissue loss, tissue reconstruction or rebuilding, tissue reinforcement (e.g., to prevent or delay progression of tissue damage or loss of tissue) or to assist in the implantation of surgical devices (e.g., bone grafts can be used to help bone heal around surgically implanted devices such as joint replacements, plates or screws). In some embodiments, a subject has a tissue defect or tissue loss caused by injury, disease, birth defect, trauma or infection.

In some embodiments, the invention provides a method of repairing or replacing a tissue defect, tissue loss or tissue damage, comprising transplanting a tissue graft according to the present invention into a subject so as to repair or replace the tissue defect, tissue loss or tissue damage in the subject. In some embodiments, the tissue graft will have a size and shape corresponding to that of the tissue being repaired or replaced. Tissue grafts according to the present invention can be prepared using the segmental additive tissue engineering or SATE methods provided herein. Thus, in some embodiments, a tissue graft according to the present invention may comprise, consist of, or consist essentially of, two or more tissue graft segments, wherein the tissue graft segments have a thickness of less than about 1 centimeter, or a thickness of about 0.3 millimeters to about 10 millimeters. In some embodiments, such a tissue graft may be an autograft (also referred to as an autogenous, autogeneic or autogenic graft), such as where the subject's own cells or tissue (e.g., autologous cells or tissue) are used to generate the tissue graft. In some embodiments, the tissue graft is an allograft (e.g., the tissue graft is generated from cells or tissues obtained from a donor subject of the same species as the recipient subject), such as where the donor and recipient subjects have been matched, for example, by HLA-matching. In some embodiments, the tissue graft is a xenograft (e.g., the tissue graft is generated from cells or tissues obtained from a donor subject of a different species as the recipient subject). For example, a tissue graft comprising human tissue may be transplanted into a non-human mammal, such as a sheep, for example for performing certain in vivo testing, etc.

A tissue graft prepared according to the present invention and transplanted into a subject can be anchored or attached or secured to existing structures (e.g., tissue) in the subject by any suitable method capable of securing tissue, such as described above. In some embodiments, the transplanted tissue graft is secured by an adhesive, stitches or sutures, staples, plates, pins or the like. In some embodiments, the means to secure the tissue graft inside the subject's body will be biocompatible or resorbable or both.

Model Systems and Screening Methods

In some embodiments, the present invention provides model systems for studying various biological processes or biological properties, and screening methods for testing the effects of various agents on such biological processes and/or biological properties. In some embodiments such biological processes may include, for example, those associated with a disease or disorder or those associated with a surgical procedure. In some such embodiments such biological processes or properties may include, for example, those associated with formation of biological tissues (including, but not limited to production of tissue grafts), such as those relating to the differentiation or culture of various cell types, or those relating to the ability of various cell types to form functional tissues, or those relating to the biological, mechanical, immunological, or other biological properties of a tissue (or tissue graft), and the like. For example, the methods, compositions (e.g. tissue grafts), and devices (e.g. bioreactors), described herein can be used in, or in conjunction with, model systems, such as model systems for studying particular diseases or disorders, or model systems for studying the ability of cells, such as stem cells (e.g. iPSCs) to form functional tissues. Similarly, the methods, compositions (e.g. tissue grafts), and devices (e.g. bioreactors), described herein can be used in, or in conjunction with, screening systems, for studying the effects of one or more agents (such as drugs, or any other agents) on the ability of cells to form functional tissues, such as tissue grafts. For example, in one embodiment, the present invention provides a method of identifying an agent that may be useful for treating, preventing or delaying the progression of a disease or disorder, or for supporting the formation of a particular tissue (for example from stem cells), or for producing a tissue graft having one or more desired properties, comprising (a) contacting a tissue graft according to the present invention with a test agent in vitro or in vivo, and (b) assessing the effects of the test agent on the tissue graft and/or on one of the biological processes or properties described above. Some such methods may also comprise contacting a tissue graft with a control agent, and comparing the effects of the test agent to that of the control agent. In some such embodiments, the tissue graft comprises cells derived from progenitor cells, pluripotent cells (such as induced pluripotent stem cells), autologous cells (such as the subject's own cells), or any cell capable of (i) forming the desired tissue(s), or (ii) differentiating into a cell that is capable of forming the desired tissue(s). In some embodiments, the tissue graft can be a vascularized tissue graft, wherein the tissue graft comprises endothelial cells or other blood vessel cells, such as those derived from progenitor cells (such as endothelial progenitor cells), pluripotent cells (such as induced pluripotent stem cells), autologous cells (such as the subject's own cells), or any cell capable of (i) forming endothelium and/or blood vessels, or (ii) differentiating into a cell that is capable of forming endothelium and/or blood vessels. In some embodiments, the tissue grafts are generated using induced pluripotent stem cells. In some embodiments, the tissue grafts comprise cells derived from a subject having a particular disease or disorder. In some embodiments, a vascularized tissue graft according to the invention can be used in, or in conjunction with, model systems, such as model systems for studying vascular diseases or disorders. In some embodiments, a vascularized tissue graft according to the invention may be used in, or in conjunction with, screening systems for studying the effects of one or more agents (such as drugs, or any other agents) on the vascularized tissue.

In some embodiments, the present invention provides a model system comprising a tissue graft according to the present invention. For example, in some embodiments the present invention provides a model system comprising a tissue graft according to the present invention that has been implanted into a subject that is a non-human mammal. In one such embodiment, the non-human mammal is a sheep. In some embodiments, the present invention provides a model system comprising a tissue graft or tissue segment according to the present invention that is used to determine whether a test material is suitable for implantation into a subject. For example, in some such embodiments, a test material may be screened or tested for desired properties, such as biocompatibility, mechanical properties, or toxicity. In some such embodiments, a test material may be a synthetic material or a natural material or a mix of synthetic and natural materials. Model systems provided by the invention can be used for various purposes such as but not limited to screening or testing materials for implantation and to study diseases under defined tissue-specific conditions, including for understanding underlying mechanisms, defining therapeutic targets and conducting compound screening, and the like.

Furthermore, those of ordinary skill in the art will appreciate that the methods, compositions (e.g. tissue grafts), and devices (e.g. bioreactors), described herein can be used in, or in conjunction with, a variety of different model systems and screening methods.

Subjects

In some embodiments the cells used in producing the tissue grafts of the present invention may be obtained from or derived from any subject, as needed or as desired. In some embodiments the methods (e.g. treatment methods) and compositions (e.g., tissue grafts) provided by the present invention may be used in any subject, as needed or as desired (for example, to repair a pathological or traumatic tissue defect, or for cosmetic or reconstructive purposes). In some embodiments, the subject is a human. In some embodiments, the subject is a mammal including but not limited to a non-human primate, sheep, or rodent (such as a rat or mouse). In some embodiments, a first subject is a donor subject and a second subject is a recipient subject. In some such embodiments the donor subject, or cells of the donor subject, may be matched to the recipient subject or cells of the recipient subject, for example, by HLA-type matching.

Vascularized Bone Grafts

In one embodiment, the present invention provides a method of preparing a vascularized bone graft, comprising: (a) obtaining a three-dimensional model of a bone portion; (b) partitioning the three-dimensional model of step (a) into two or more bone segment models; (c) preparing two or more bone graft segments, comprising: (i) obtaining a scaffold having a size and shape corresponding to each of the bone segment models of step (b); (ii) obtaining a bioreactor having an internal chamber configured to hold the scaffold; (iii) applying to the scaffold (1) bone-forming cells, or cells capable of differentiating into bone-forming cells, and (2) blood vessel-forming cells, or cells capable of differentiating into blood-vessel forming cells; (iv) culturing the cells on the scaffold within the bioreactor to form a bone graft segment; and (v) removing the bone graft segment from the bioreactor; and (d) assembling the two or more bone graft segments prepared in step (c) to form a bone graft having a size and shape corresponding to the bone portion of step (a). In one embodiment, the cells applied to the scaffold in (c) (iii) comprise pluripotent cells, induced pluripotent cells, progenitor cells, differentiated cells, or any combination thereof. In one embodiment, the cells of (c) (iii) (1) comprise bone marrow stromal cells or mesenchymal stem cells or pluripotent cells induced toward mesenchymal lineage or differentiated bone cells or any combination thereof. In one embodiment, the cells of (c) (iii) (2) comprise endothelial progenitor cells or pluripotent cells induced toward endothelial lineage or differentiated endothelial cells or any combination thereof. In one embodiment, the bone graft segment has a thickness of about one centimeter or less. In one embodiment, the bone graft segment has a thickness of about 0.3 millimeters to about 10 millimeters. In one embodiment, the assembling of the bone graft segments is carried out with an adhesive, one or more pins and holes, or both. In one embodiment, the pins are metallic or resorbable. In one embodiment, the pins are titanium. In one embodiment, the adhesive is a biocompatible bone glue, for example, a polymer such as NovoSorb (PolyNovo Biomaterials, Melbourne) or any gel, liquid, rubber-like substance or any other biocompatible material capable of securing together two or more bone segments. Examples of bone glues include, but are not limited to, polymer based bone glues such as polyurethane-based and polymethylmethacrylate-based bone glues. In one aspect, the invention provides a method of repairing or replacing a bone portion in a subject, comprising steps (a)-(d) described above, and further comprising transplanting the bone graft into a subject so as to repair or replace the bone portion in the subject.

In one aspect, the invention provides a vascularized bone graft prepared by a method of the invention. In another aspect, the invention provides a vascularized bone graft for repairing or replacing a bone portion in a subject, wherein the bone graft comprises two or more bone graft segments, wherein the two or more bone graft segments are connected together to form a vascularized bone graft having a size and shape corresponding to the bone portion to be replaced or repaired. In some embodiments, the bone graft segments comprise bone cells derived from progenitor cells (such as mesenchymal progenitor cells), pluripotent cells (such as induced pluripotent stem cells), autologous cells (such as the subject's own cells), or any cell capable of (i) forming bone, or (ii) differentiating into a cell that is capable of forming bone. In some embodiments, the bone graft segments comprise endothelial or blood vessel cells derived from progenitor cells (such as endothelial progenitor cells), pluripotent cells (such as induced pluripotent stem cells), autologous cells (such as the subject's own cells), or any cell capable of (i) forming endothelium and/or blood vessels, or (ii) differentiating into a cell that is capable of forming endothelium and/or blood vessels. In some embodiments, each bone segment has a maximum thickness of less than about one centimeter, or has a maximum thickness of about 0.3 millimeters to about 10 millimeters.

In some embodiments the cells used in accordance with the above methods, or used in the manufacture of the above bone grafts, are derived from, or derived from a cell obtained from, the same subject into which the bone graft is to be placed such that they are autologous cells, or are derived from autologous cells. In one embodiment, the cells are derived from pluripotent stem cells, such as, for example, induced pluripotent stem cells, embryonic stem cells, cloned stem cells, or adult stem cells (such as bone marrow stem cells). In some embodiments the induced pluripotent stem cells may be derived from a somatic cell taken from the same subject into which the bone graft is to be placed or from a suitably matched donor, such as HLA-matched. In some embodiments, the cells are mesenchymal stem cells and/or endothelial progenitor cells. In some embodiments, the cells are seeded onto the scaffold at a cell ratio of 1:1, or any ratio from about 2:8 to about 8:2.

In some embodiments, the present invention provides culture vessels suitable for use in the manufacture of bone grafts, such as bioreactors described herein. Such culture vessels may be perfusion bioreactors comprising one or more custom-designed graft chambers into which a cell/scaffold construct can be inserted and cultured under press fit conditions. Bioreactors may comprise a top element and a bottom element, wherein the top element and the bottom element are secured together. In one embodiment, the top element comprises a reservoir for culture medium, a fluid outlet port and one or more fluid channels. In one embodiment, the bottom element comprises a fluid inlet port and one or more fluid channels. In one embodiment, the culture vessel is generated using computer-assisted manufacturing. In one embodiment, the computer-assisted manufacturing comprises a computer-numerical-control milling machine and/or three-dimensional printing.

In some embodiments, the graft chamber may be a custom-shaped chamber(s) that accommodates the scaffold/cell construct(s) until maturation of functional bone. In some embodiments, a graft chamber is of a size sufficient to accommodate a segment of bone having a thickness of about 0.3 millimeters to about 10 millimeters.

In some embodiments, the scaffold and/or bone segment may be positioned in the graft chamber using frames or inserts. Frames or inserts may be used to customize the size and shape of a graft chamber and position the scaffold and/or bone segment in the graft chamber, as desired, to culture the bone segment under direct perfusion, press-fit conditions to maximize the flow of fluid through the scaffold and/or bone segment, and minimize the flow of fluid around the scaffold and/or bone segment. In some embodiments the graft chamber may have a generic shape or size, but a frame(s) or insert may be used to customize the size and shape (e.g. the internal size and shape) of the graft chamber, as desired, to accommodate the scaffold and/or bone segment. Frames or inserts may be made of any suitable material, for example, a biocompatible, non-toxic, moldable plastic.

In one embodiment the present invention provides scaffolds suitable for use in the manufacture of bone grafts, for example as described herein. In one embodiment, the scaffold is generated using computer-assisted manufacturing. In another embodiment, the manufacturing comprises a computer-numerical-control milling machine, casting technologies, laser cutting and/or three-dimensional printing. In one embodiment, the scaffold consists essentially of decellularized bone tissue. In one embodiment, the scaffold comprises a synthetic ceramic/polymer composite material. In one embodiment, the scaffold consists essentially of a material capable of being absorbed by cells.

In some embodiments, the invention provides a model system for bone diseases or disorders and/or vascular diseases or disorders, the model system comprising a vascularized bone graft according to the invention. In one aspect, the invention provides a model system for bone deficiencies, defects, diseases or disorders, the model system comprising a vascularized bone graft comprising two or more bone graft segments, wherein the two or more bone graft segments are connected together to form a bone graft. In one aspect, the invention provides a method of identifying a compound that may be useful for treating a bone deficiency, defect, disease or disorder, comprising (a) contacting a bone graft, in vivo or in vitro, with a test agent, wherein the bone graft comprises two or more bone graft segments, wherein the two or more bone graft segments are connected together to form a bone graft; and (b) determining whether the test agent improves the function of, or improves the growth of, or prevents or delays degeneration of the bone graft of (a). In some embodiments the bone deficiency, defect, disease or disorder comprises congenital, pathological or traumatic defects, cosmetic procedures, degenerative disorders, surgical resection following neoplastic transformation, or chronic infection. In one aspect, the invention provides a method of identifying a compound that may be useful for treating a vascular disease or disorder, comprising (a) contacting a vascularized bone graft, in vivo or in vitro, with a test agent, wherein the vascularized bone graft comprises two or more vascularized bone graft segments, wherein the two or more vascularized bone graft segments are connected together to form a vascularized bone graft; and (b) determining whether the test agent treats or prevents or delays the progression of the vascular disease or disorder. In some embodiments, the bone graft segments comprise bone cells derived from progenitor cells (such as mesenchymal progenitor cells), pluripotent cells (such as induced pluripotent stem cells), autologous cells (such as the subject's own cells), or any cell capable of (i) forming bone, or (ii) differentiating into a cell that is capable of forming bone. In some embodiments, the bone graft segments comprise endothelial or blood vessel cells derived from progenitor cells (such as endothelial progenitor cells), pluripotent cells (such as induced pluripotent stem cells), autologous cells (such as the subject's own cells), or any cell capable of (i) forming endothelium and/or blood vessels, or (ii) differentiating into a cell that is capable of forming endothelium and/or blood vessels. In some embodiments, each bone segment has a maximum thickness of less than about one centimeter, or has a maximum thickness of about 0.3 millimeters to about 10 millimeters.

Various embodiments of the present invention may also be further described by the following non-limiting Examples.

Example

Engineering Vascularized Bone Grafts for Repairing Large Skeletal Defects

Introduction

Bone deficiencies resulting from trauma, birth defects and diseases affect an increasing number of patients worldwide, with a combined annual U.S. market for bone repair and regeneration therapies projected to reach 3.5 billion by 2017. Current treatments for these patients, which rely on the implantation of alloplastic materials or transplantation of bone tissue, are not optimal and alternative therapeutic strategies are required to restore skeletal integrity and functionality in a large number of clinical cases.

Figure 2:
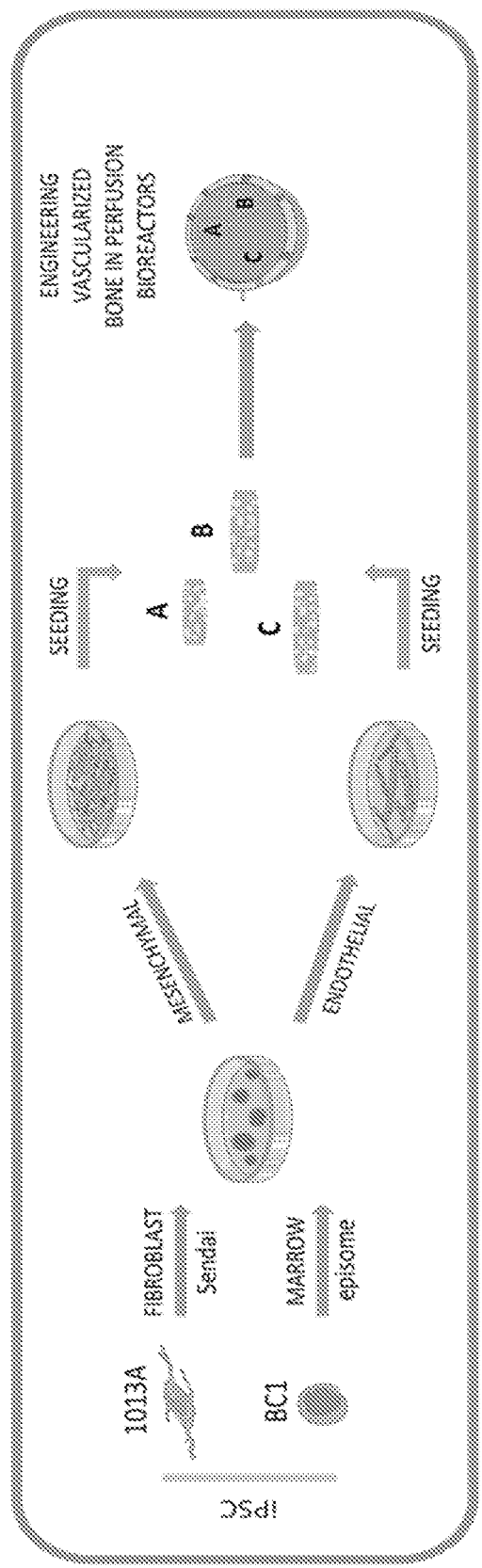
FIG. 2. Osteogenic and vascular progenitors are generated from hiPSC and co-cultured onto custom-made osteoinductive scaffolds (here, on three scaffolds labeled A, B and C) in perfusion bioreactors.
Figure 3:
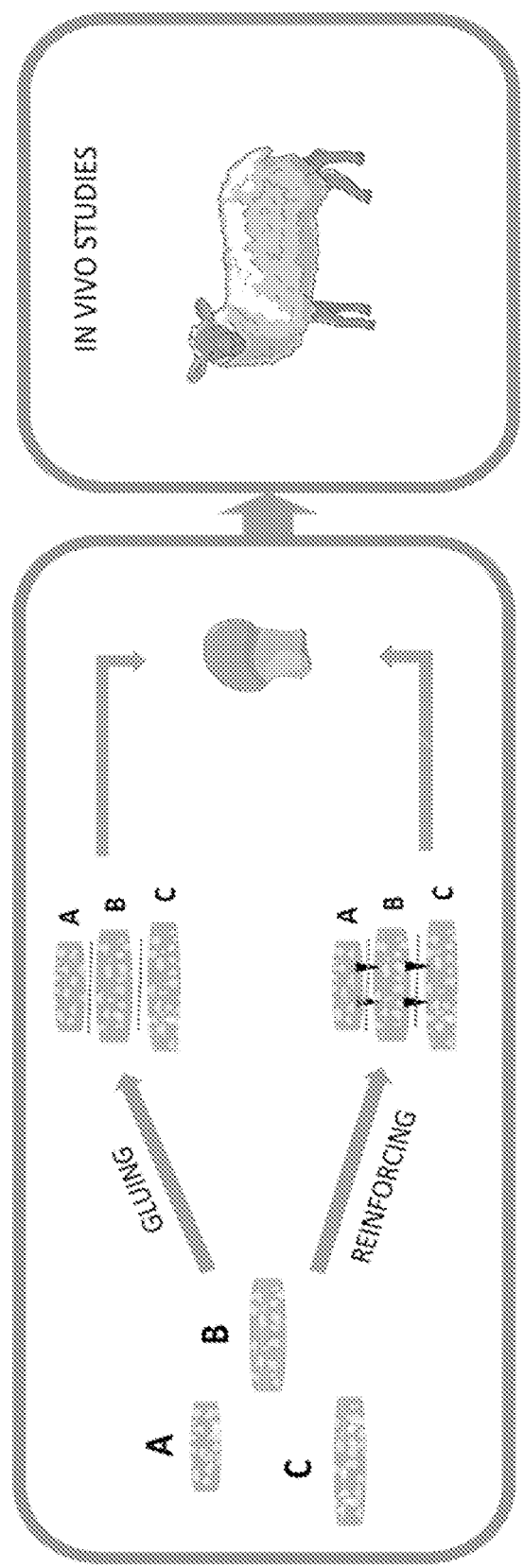
FIG. 3. Engineered vascularized bone segments (here, three segments labeled A, B and C) are assembled using biocompatible bone glues and/or reinforced using 3D printed titanium pins and holes. Additional studies can be designed to repair clinically relevant skeletal defects in large animals.

This Example proposes a strategy for engineering vascularized bone grafts from human induced pluripotent stem cells (hiPSCs) for enhanced healing of complex skeletal defects. In particular, the ability to derive autologous osteogenic and vascular cells constituting healthy bone from hiPSCs for any patient in virtually unlimited numbers represents an unprecedented therapeutic resource. Vascularized bone substitutes will be engineered using a biomimetic scaffold-bioreactor approach of bone development. Computer-aided and rapid prototyping technologies will allow the preparation of bone substitutes of any shape and size. Digital models of large bone defects will be created and then segmented in complementary sub-parts that will be used to produce customized biomaterial scaffolds and bioreactors via computer-aided design and manufacturing technologies, such as 3D printing (see FIG. 1). The proposed engineering strategy overcomes the limitations associated with perfusion culture of large bone grafts. Mesenchymal and endothelial progenitor cells will be derived from hiPSCs generated using any available reprogramming method, and then combined with compliant scaffolds and cultured in perfusion bioreactors until maturation of functional vascularized tissue (see FIG. 2). Engineered bone segments will then be assembled together (lego-like approach) using a biocompatible bone glue, and/or reinforced using 3D printed titanium holes and pins to match the shape and dimension of the original defect. Future studies will be aimed at exploring the therapeutic potential of hiPSC-engineered bone using different animal models of complex skeletal defects (see FIG. 3).

Engineering large and geometrically defined vascularized bone grafts from hiPSCs represents a novel solution for the treatment of skeletal defects characterized by severe bone loss, and opens the opportunity to provide personalized therapies to a large number of patients. As importantly, such bone grafts represent qualified models to study bone development and pathologies, as well as screening new drugs and test biomaterials.

The Example describes studies designed to engineer vascularized bone grafts from human induced pluripotent stem cells (hiPSC) for enhanced healing of skeletal defects. Patient-specific bone grafts will be engineered using a biomimetic scaffold-bioreactor approach of bone development in vitro, and customized to meet specific clinical needs with the aid of computer-assisted and rapid prototyping technologies. Engineering patient-specific customized bone grafts could be used to develop innovative treatments to restore skeletal integrity and functionality in clinical situations characterized by severe bone loss.

Skeletal reconstructive therapies are needed to obviate bone deficiencies associated with, for example, reconstruction of congenital (1) and traumatic (2) skeletal defects, cosmetic procedures, degenerative disorders and surgical resection following neoplastic transformation (3) and chronic infection (4). The worldwide market for bone replacement and repair therapies is massive (5, 6), and the need for bone tissue substitutes constantly increasing due to the rapid growth of human population and extension of life expectancy (7, 8). Today, the number of elderly reporting age-related fractures is estimated to be over 100 million per year worldwide (9-11), and this number is projected to constantly increase during the next decades, with the number of elderly people (+65 years) estimated to be about 2 billion by 2050 (12). New approaches are therefore required to develop effective therapies for complex bone reconstructions. Biomimetic tissue engineering strategies have recently been explored for the ex vivo cultivation of functional bone substitutes by interfacing osteocompetent cells to biomaterials under appropriate culture conditions in bioreactors, which provide mechanical stimulation and a proper environment that guide functional tissue maturation. Attempts to engineer geometrically defined bone substitutes have been reported recently, culturing human mesenchymal stem cells in an osteoinductive scaffold-perfusion bioreactor system (13). However, restrictions associated with 1) the limited regenerative potential of stem cells derived from adult tissues, 2) lack of vascularization and 3) culture of large bone substitutes in direct perfusion bioreactors were not addressed, but all affect the ability to engineer functional grafts for enhanced healing of large and complex skeletal defects. In particular, engineering large cell/scaffold constructs is cumbersome using direct perfusion bioreactors, due to the resistance provided by the large constructs to the flow. The development of new tissue inside the scaffold progressively limits the perfusion of the fluid through the construct, with negative consequences on the functionality of the perfusion system. Independent studies demonstrated that a similar scenario could be seen when culturing 4×4 mm constructs in direct perfusion bioreactors for 5 weeks.

This Example proposes studies to engineer vascularized bone substitutes from hiPSCs, and adopt a combination of medical imaging procedures, computer-aided technologies and rapid prototyping to allow the construction of clinically relevant bone substitutes in perfusion bioreactors. The strategy represents a novel and innovative solution to cope with the burden of bone deficiencies, whose clinical translation will have profound social impact by improving the health status and quality of life of many patients. These studies will also provide new insights into hiPSC biology, which are critical to understand functional differentiation of pluripotent stem cells into mature tissues and organs. Additionally, hiPSC-engineered vascularized bone grafts would provide valuable high-fidelity models to investigate tissue development in normal and pathological conditions, and test new pharmaceuticals and biomaterials within a context that resembles several aspects of the native bone environment.

Background

Bone displays intrinsic capacity to regenerate and self-repair but this ability is limited to small fractures and reconstructive therapies are needed in a large number of clinical conditions to restore tissue integrity and functionality (14). Current treatments are based on the transplantation of autogeneic and/or allogeneic bone grafts, or implantation of graft materials with osteoconductive and osteoinductive properties. Autogeneic bone grafts represent the gold standard treatment for bone replacement procedures, due to immune tolerability and provision of essential components supporting bone regeneration and repair, but limited availability and donor site morbidity often restrict their clinical use (15). On the other hand, allogeneic decellularized bone grafts are available in large amounts but integrate slowly (16), carry the risk of infection transmission and may display immune incompatibility leading to transplant rejection (17). Implantation of alloplastic materials overcomes some of the restrictions encountered with autogeneic and allogeneic grafts, including disease transmission, complex shape and availability, but display poor integration, frequently result in biomaterial-associated infection, and lack biological functionality and mechanical compliance, leading to implant failure and substitution (18). Bone tissue engineering represents a promising therapeutic solution, since it opens the possibility to engineer an unlimited amount of viable bone substitutes to meet specific clinical needs (19). Human mesenchymal stem cells (hMSC) derived from adult tissues have been extensively used for bone engineering applications with encouraging results, but exhibit restricted potential for clinical applications due to limited availability, inadequate regenerative potential and decrease in functionality associated with in vitro expansion and donor age (20-23).

Autologous bone substitutes in the size range of ~1 cm have been grown from adult stem cells and used to facilitate bone healing in experimental animals and in humans (24, 25). However, their scale-up to clinical sizes and functionality are limited due to the lack of blood supply, and limited proliferation and vasculogenic potential of cultured adult stem cells. An appropriate blood supply has been recognized as an essential component of normal fracture healing and defective angiogenesis at the fracture site has been a primary consideration when poor outcomes occur (26). Poor blood supply leads to hypoxia and necrosis of the grafted tissue, and can result in decreased bone formation ("atrophic bone"). Similarly, implantation of large cellularized bone substitutes without the connection to vascular supply can result in cell death in the interior regions of the transplant. To expedite cell survival and bone regeneration, recent tissue engineering approaches have involved transplantation of endothelial progenitors or vascular networks within bone substitutes (27-29). Studies have shown the positive effects of endothelial cells and osteogenic cells in direct co-culture model (30, 31). In addition, studies suggest that co-transplantation of endothelial cells and BMSC promoted new bone formation in vivo (28), and that endothelial networks engineered within bone substitutes can functionally anastomose with the host vasculature (27, 32).

Pluripotent stem cells display high regenerative potential and ability to differentiate toward all specialized cells constituting healthy bone tissue (33, 34). When derived using nuclear reprogramming technologies, pluripotent stem cells allow the construction of patient-specific bone substitutes for personalized applications. Both mesenchymal and endothelial progenitor cells have recently been derived from pluripotent stem cells (35-40), opening new opportunities for the unlimited construction of vascularized bone substitutes for enhanced reconstructions of large skeletal defect. It is therefore important to explore the possibility to engineer vascularized bone grafts from induced pluripotent stem cells, in order to develop safe and effective treatments for many patients affected by severe skeletal defects and bone disorders.

Results

The inventors have extensive experience with cultivation of bone substitutes from mesenchymal stem cells derived from adult tissues and from human pluripotent stem cells. A set of studies exploring the relative regenerative potential of hMSCs and mesenchymal progenitors derived from human embryonic stem cell (hESC) lines have demonstrated comparative advantages of hESC-derived mesenchymal progenitors for bone engineering applications (20, 35, 36). Studies in monolayer and 3D cultures on scaffolds in bioreactors have shown that hESC-derived mesenchymal progenitors highly resemble hMSCs in terms of morphology, surface antigen and global gene expression profile, but display higher proliferation potential, biosynthetic activity and mineralization properties, all paramount features for the unlimited construction of functional substitutes for bone engineering applications. The derivation protocol has been extended to hiPSC lines generated from different tissues and using different reprogramming technologies based on non-integrating vectors, opening the possibility to engineer safe patient-specific bone substitutes for personalized applications. hiPSC lines were characterized by immunohistochemistry to assess pluripotency and karyotyped, before being induced toward the mesenchymal lineage for 7 days. Mesenchymal-like phenotype was characterized by flow cytometry and by probing surface marker expression and differentiation potential in monolayer (osteogenesis, adipogenesis) and pellet cultures (chondrogenesis). Differentiation toward the osteogenic lineage was confirmed by alkaline phosphatase and mineralization, differentiation toward the chondrogenic lineage was shown by glycosaminoglycans, and differentiation toward the adipogenic lineages was shown by lipid characterization.

Cells were then seeded on decellularized bone scaffolds (4 mm Ø×4 mm height), and cultured in osteogenic medium under constant perfusion (linear flow velocity of 800 µm/sec) for 5 weeks before 12-week subcutaneous implantation in immunocompromised mice to assess stability and further tissue maturation. Histological and immunohistochemical analyses of engineered bone were carried out following bioreactor cultivation and subcutaneous implantation in immunocompromised mice. Micrographs showed maturation of phenotypically stable bone-like tissue and vascularization. MicroCT analysis of engineered bone showed an increase in mineral density and structural parameters (41).

Altogether the results demonstrate that mesenchymal progenitors can be derived from hiPSC lines, and used to engineer mature and phenotypically stable bone tissue for repair treatments of skeletal defects in personalized applications. In all studies, perfusion bioreactors were shown to be particularly important for bone development, as they provide biomechanical stimulation to the cells (13), and support survival of the cells in the interior of the constructs, resulting in the production of thick homogenous bone-like matrix (41). Studies are now directed at developing suitable protocols for engineering vascularized bone substitutes for enhanced healing of large and geometrically complex skeletal defects. Preliminary studies have shown that functional endothelial progenitors can be derived from hESC lines. Following differentiation of embryoid bodies in controlled conditions, isolated CD34 positive cells were able to specifically internalize DiI-Ac-LDL and form tubes when plated on Matrigel. This approach is being translated to hiPSCs for the construction of patient-specific multicellular composite bone substitutes.

In addition, preliminary vascularization studies in 3D cultures have shown that co-culture of hiPSC-derived mesenchymal progenitors and human bone marrow stromal cells (BMSC) with human umbilical vein endothelial cells (HUVEC) result in long-lasting formation of vascular networks, both when cells are embedded in fibrin clots or seeded onto decellularized bone scaffolds, which represent more compliant substrates for skeletal repair treatments. Interestingly, number and stability of vascular structures were similar when HUVEC were cultured with hiPSC-derived mesenchymal progenitors and human BMSC in fibrin clots. Epifluorescence micrographs showed the presence of stable 3D vascular networks 3 weeks after seeding. Hematoxylin/Eosin staining of clot cross sections showed the presence of hollow vessels across the entire construct for both co-culture of mesenchymal progenitors derived from hiPSC line 1013A and BMSC with HUVEC 4 weeks after seeding. To follow the formation of vascular network in vitro, cell populations were specifically labeled with different Vybrant tracker dyes before embedding in fibrin clots, and cultured for 4 weeks in a mixture of osteogenic and endothelial inducing media before harvesting for histological analysis. No vascular structures were observed when HUVEC were cultured alone, suggesting the pivotal role of mesenchymal cells to support and guide tissue vascularization. Studies can be carried out to identify the molecular mechanism underlying this finding in order to develop improved protocols to support maturation of vascularized bone tissue in vitro.

Similar outcomes were observed when cells were seeded onto decellularized bone scaffolds (8 mm Ø×2 mm height) and cultured for 6 weeks under osteogenic- and vascular-inducing conditions. The maturation of bone-like tissue, evidenced by the positive staining for osteocalcin, osteopontin and bone sialoprotein, was accompanied by the formation of networks of hollow vessels inside the constructs. Immunohistochemical examination showed that the tubular structures were positive for the endothelial marker CD31.

Different seeding ratios, and culture conditions can be tested to explore the potential to enhance the formation of vascularized bone tissue, as well as to assess the potential of other hiPSC lines for engineering vascularized bone grafts. Future studies are aimed at exploring the effect of dynamic conditions in perfusion bioreactors on the vascularization process. Development of proper vascularization protocols, in combination with the biomimetic osteoinductive scaffold-perfusion bioreactor approach, will allow the construction of vascularized bone grafts for personalized repair treatments of complex skeletal defects.

Research Design and Methods

This Example proposes the engineering of vascularized bone grafts from hiPSCs using a stepwise differentiation approach, starting with derivation of lineage-specific osteogenic and endothelial progenitors, and subsequent co-culture of these progenitors in a "biomimetic" scaffold-bioreactor model, which ensure controlled development of functional bone tissue in vitro. Computer-aided and rapid prototyping technologies will be employed to enable the fabrication of custom-made bone substitutes for the reconstruction of large and geometrically complex skeletal defects. Engineering patient-specific custom-made bone grafts can be used to develop innovative treatments to restore skeletal integrity and functionality in clinical situations characterized by severe bone loss. This Example describes three sub-projects as described below.

1. Computer-aided design (CAD) of skeletal models and computer-aided manufacturing (CAM) of biomaterial scaffolds and perfusion bioreactors. The objective of Part 1 is to create and elaborate digital models of skeletal defects to guide the design and manufacturing of customized biomaterial scaffolds and perfusion bioreactors. Digital models of skeletal defects will be created and segmented into complementary sub-parts using CAD software, then these models will be used as a reference for the computer-aided fabrication of biomaterial scaffolds of corresponding size and shape and custom-made perfusion bioreactors. Bioreactors will be machined and/or free-form fabricated using the digital models in order to accommodate each specific cell/scaffold construct in a press-fit fashion and allow culture under direct perfusion.

Digital models of skeletal defects will be created using CAD software (e.g., Autocad, Solidworks, ProE, Creo). To validate the therapeutic potential of the proposed engineering strategy, this approach can be extended to defect models of different size and shape. Reference models of skeletal defects in CAD will be edited and segmented into smaller complementary sub-parts (lego-like building parts) that can be cultured in perfusion bioreactors without affecting the perfusion system. The segmented bone sample files will then be saved in compatible IGES or SLT formats and imported in CAM software (e.g., SprutCAM). The generated files in CAM software will then be processed to generate the appropriate G-Codes to drive a computer-numerical-control (CNC) milling machine (e.g., Tormach, Bridgeport), select appropriate machining tools bits and program the machining paths to cut the scaffolding materials into the desired segmented shapes. Plugs of trabecular bone (cow and/or human) of adequate size will be drilled, cleansed under high-pressure streamed water to remove the bone marrow, and then sequentially washed to remove cellular material as previously described (41). Decellularized bone plugs will then be freeze-dried, and used for the fabrication of scaffolds corresponding to the shape and size of the segmented samples of the skeletal defect. The potential to use synthetic, resorbable and mechanically compliant ceramic/polymer composite materials will be explored in parallel, since it represents an essential requisite for the reproducible and large-scale fabrication of bone substitutes for clinical applications. Fabricated scaffolds will be sterilized and conditioned in culture medium overnight prior to cell seeding. The segmented bone sample files edited in CAD will then be used to design customized bioreactor, which can accommodate the cell/scaffold construct(s) in a press-fit fashion under direct perfusion conditions. Again, the CAD files will be converted into compatible formats and imported into CAM and/or 3D printer software, and used to fabricate the bioreactors using different plastic materials. Each bioreactor will be constituted of two parts (top and bottom) that will be secured together, for example, by means of metallic screws. The cell/scaffold constructs will be cultured in between the top and bottom elements. The bottom part will include key elements including but not limited to the inlet port and channels for flow perfusion, as well as anatomically shaped chambers to accommodate the cell/scaffold constructs. The top part will include elements such as a medium reservoir and the outlet port for flow perfusion. A system of tubes can be used to connect the inlet and outlet ports and allow perfusion throughout the bioreactors via the control of a peristaltic pump.

2. Engineering vascularized bone in custom-made perfusion bioreactors. The objective of Part 2 is to engineer vascularized patient-specific bone grafts in vitro. hiPSC lines reprogrammed from different tissues using non-integrating vectors will be induced toward the mesenchymal and endothelial lineage prior to culture under biomimetic conditions in the osteoinductive scaffold-perfusion bioreactor system to guide maturation of functional vascularized bone tissue.

hiPSC reprogrammed using non-integrating vectors from different donors and source tissues (line BC1 and 1013A) will be expanded, characterized for pluripotency and karyotyped before induction toward the mesenchymal and endothelial lineages. Derived progenitor cells will be expanded, characterized by flow cytometry, and karyotyped to assess genetic normality. Qualitative and quantitative methods will be used to evaluate osteogenic and endothelial phenotype in vitro, including histological and immunohistochemical examination, biochemical and morphological assays, and gene expression analysis. Vascular induction will be tested in monolayer cultures and embryoid bodies, in the presence of specific factors (BMP-4, activin, bFGF, VEGF). Differentiated progenitors will be sorted based on surface antigen expression (CD34, CD31, KDR, C-KIT) and cultured in endothelial media. Progenitor yield, viability, proliferation and phenotype-expression of specific markers (CD31, vWF, VE-cadherin, SMA) will be assessed by flow cytometry, immunofluorescence and gene expression. Network formation and sprouting will be tested by encapsulation in collagen/fibronectin/Matrigel before co-cultivation studies. Commercially available BMSC (Lonza) and HUVEC (Lonza) will be used as reference lines to assess the quality and functionality of hiPSC-derived mesenchymal and endothelial progenitors. To engineer vascularized bone tissue, hiPSC-derived mesenchymal and endothelial progenitors will be co-seeded onto decellularized bone scaffolds (or others) and cultured in bioreactor in a mix of osteogenic and endothelial medium. Pre-differentiation, cell seeding ratios, concentration of differentiation factors and use of fibrin sealants will be explored to design optimal culture conditions for the development of fully vascularized bone grafts in vitro. Culture in bioreactors will be conducted for a period of 3-5 weeks, until the formation of a mature vascularized tissue. Tissue development will be assessed using qualitative and quantitative methods, including histological and immunohistochemical examination, biochemical assays, high-resolution characterization techniques (SEM, FIB-TEM, Tof-SIMS), imaging procedures (microCT) and mechanical testing (Young's modulus, tensile and compressive strength).

3. Gluing of engineered bone segments and evaluation of stability. The objective of Part 3 is to fabricate custom-made bone grafts for complex skeletal reconstruction. Engineered vascularized bone segments will be assembled to match the shape of the skeletal defect by means of a biocompatible bone glue, or reinforced using 3D printed metallic (for example, titanium) or resorbable pins and holes. Future studies will be aimed at exploring safety and efficacy of engineered bone in animal models of critical-sized skeletal defects (both in loading and non-loading anatomical locations).

Engineered bone segments will be assembled to match the shape of the model of skeletal defect by means of a biocompatible bone glue for welding large bone grafts or reinforced using 3D printed metallic (for example, titanium) or resorbable pins and holes. Future studies will be aimed at exploring the safety and regenerative potential of engineered bone in animal models of complex critical sized skeletal defects (both in loading and non-loading skeletal locations). For example, digital models of femoral head defects in adult animals will be created using medical imaging procedures (CT scan) and 3D images processed and segmented (as described above) and used to engineer vascularized bone as described herein. Femoral head ostectomy will then be performed in the animals to remove the femur head to an extent matching the digital model generated (as described above), and the engineered vascularized bone place in site to restore skeletal integrity and functionality. Tissue development, healing and quality of regenerated tissue will be evaluated in vivo using medical imaging procedures and following explantation using histological and immunohistochemical techniques, high-resolution characterization techniques (e.g., SEM, FIB-TEM, Tof-SIMS), and mechanical testing (e.g., Young's modulus, tensile and compressive strength).

As described herein, vascularized bone grafts can be engineered using osteogenic and endothelial progenitors derived from human induced pluripotent stem cells for personalized reconstructive therapies. Although endothelial progenitors can be derived from both hESCs and hiPSCs (38-40), the derivation efficiency is low and the derived progenitors display scarce proliferation ability, which limits the possibility to generate enough cells for engineering large vascularized bone substitutes. To speed up the development of suitable vascularization protocols, in parallel to optimizing the derivation of highly proliferative endothelial progenitors from hiPSCs, commercially available HUVECs can be used, and then the protocols can be translated to endothelial progenitors derived from hiPSCs. The hiPSC-derived mesenchymal progenitors may be expanded to a required amount before induction toward the endothelial lineage, and then used to engineer vascularized bone substitutes.

As described herein, the engineered bone substitutes can be assembled to match the shape of the skeletal defect using a biocompatible bone glue for welding large bone grafts, which might be insufficient to ensure a stable connection following implantation in high load-bearing locations. To solve this problem, alternative solutions will be tested, including reinforcement using 3D printed metallic or resorbable pins and holes.

Human Stem Cells

A stepwise protocol is proposed for preparation of vascularized bone grafts from human iPSCs, which will include: (a) Differentiation and expansion of osteogenic and vascular progenitors from human iPSCs, and testing their functional potential for new tissue formation; (b) Preparation and seeding of decellularized bone scaffolds or any other biocompatible and resorbable biomaterial scaffolds; and (c) Cultivation of osteogenic tissue phase in conjunction/sequence with formation of microvascular network.

Cell lines: Human iPSC lines 1013A (derived by Sendai virus in the NYSCF laboratory) and BC1 (derived by episomal plasmid vector, from Life Technologies) can be used. Initial studies will be done in parallel with ESC line H9 (from Wicell Research Institute) and commercially available adult cells (BMSC and HUVEC from Lonza).

Sources of Materials

Human iPSC line BC1 was obtained from Life Technologies. This line, originally derived from the bone marrow of an anonymous donor, was published in *Cell Research* (18 Jan. 2011). This line is being used as a control line against which future control lines will be tested.

Human iPSC line 1013A was derived at the New York Stem Cell Foundation laboratory from a skin biopsy.

Reference BMSC and HUVEC lines are commercially available and can be purchased from Lonza.

CONCLUSIONS

The data generated from this protocol are expected to provide a proof of concept for development of vascularized bone substitutes from hiPSC. New insights will be gained into bone formation and vascularization by hiPSC cultured under biomimetic conditions, using scaffolds and bioreactors. Additionally, engineered vascularized bone substitutes would provide valuable high-fidelity models for quantitative in vitro studies of bone development and disease as well as drug screening and biomaterial testing, within a context that resembles selected aspects of the native bone environment.

References Cited in Example

Each of the references listed below, and all other references cited in this patent application, are hereby incorporated by reference in their entireties.

1. Biswas G, et al. Congenital sternal cleft. *Br J Plast Surg* 2001, 54:259-261.
2. Jaffe K A, et al. Massive bone allografts for traumatic skeletal defects. *South Med J* 1991, 84:975-982.
3. Mehrara B J, et al. Scalp reconstruction. *J Surg Oncol* 2006, 94:504-508.
4. Jia W T, et al. Free vascularized fibular grafting in combination with a locking plate for the reconstruction of a large tibial defect secondary to osteomyelitis in a child: a case report and literature review. *J Pediatr Orthop B* 2010, 19(1):66-70.
5. Hüsing B, et al. Human Tissue Engineered Products: Today's Markets and Future Prospects 2003.
6. Laurencin C, et al. Bone graft substitutes. *Expert Rev Med Devices* 2006, 3(1):49-57.
7. Greenbaum S. Longevity Rules: How to Age Well into the Future. Carmichael: ESKATON 2010.
8. Hollinger J O, et al. Options for tissue engineering to address challenges of the aging skeleton. *Tissue Eng* 2000, 6(4):341-350.
9. Kannus P, et al. Why is the age-standardized incidence of low-trauma fractures rising in many elderly populations? *J Bone Miner Res* 2002, 17(8):1363-1367.
10. Randell A, et al. Direct clinical and welfare costs of osteoporotic fractures in elderly men and women. *Osteoporos Int* 1995, 5(6):427-432.
11. Pasco J A, et al. The human cost of fracture. *Osteoporos Int* 2005, 16(12):2046-2052.
12. Commercial Opportunities from an Aging Population. Business Insights. 2004.
13. Grayson W L, et al. Engineering Anatomically Shaped Human Bone Grafts. *Proc Natl Acad Sci USA* 2010, 107(8):3299-304.
14. Braddock M, et al. Born again bone: tissue engineering for bone repair. *News Physiol Sci* 2001, 16:208-213.
15. Banwart J C, et al. Iliac crest bone graft harvest donor site morbidity. A statistical evaluation. *Spine* 1995, 20(9): 1055-1060.
16. Finkemeier C G. Bone-grafting and bone-graft substitutes. *J Bone Joint Surg Am* 2002, 84-A:454-464.
17. Delloye C. Tissue allografts and health risks. *Acta Orthop Belg* 1994, 60(1):62-67.
18. Hing K A. Bone repair in the twenty-first century: biology, chemistry or engineering? *Philos Transact A Math Phys Eng Sci* 2004, 362(1825):2821-2850.
19. Meijer G J, et al. Cell-based bone tissue engineering. *PLoS medicine* 2007, 4(2):e9.
20. de Peppo G M, et. al. Human embryonic mesodermal progenitors highly resemble human mesenchymal stem cells and display high potential for tissue engineering applications. *Tissue Eng Part A* 2010, 16:2161-2182.
21. Baxter M A, et al. Study of telomere length reveals rapid aging of human marrow stromal cells following in vitro expansion. *Stem Cells* 2004, 22:675-682.
22. Mareschi K, et al. Expansion of mesenchymal stem cells isolated from pediatric and adult donor bone marrow. *J Cell Biochem* 2006, 97:744-754.

23. Zhou S, et al. Age-related intrinsic changes in human bone-marrow-derived mesenchymal stem cells and their differentiation to osteoblasts. *Aging Cell* 2008, 7:335-343.
24. Meinel, L. et al. Silk implants for the healing of critical size bone defects. *Bone* 37, 688-698 (2005).
25. Marolt, D., Knezevic, M. & Novakovic, G. V. Bone tissue engineering with human stem cells. *Stem Cell Res Ther* 1, 10 (2010).
26. Hankenson, K. D., Dishowitz, M., Gray, C. & Schenker, M. Angiogenesis in bone regeneration. *Injury* 42, 556-561 (2011).
27. Tsigkou, O. et al. Engineered vascularized bone grafts. *Proc Natl Acad Sci USA* 107, 3311-3316 (2010).
28. Kaigler, D. et al. Transplanted endothelial cells enhance orthotopic bone regeneration. *J Dent Res* 85, 633-637 (2006).
29. Kusuma, S. & Gerecht, S. Engineering blood vessels using stem cells: innovative approaches to treat vascular disorders. *Expert Rev Cardiovasc Ther* 8, 1433-1445 (2010).
30. Villars, F. et al. Effect of HUVEC on human osteoprogenitor cell differentiation needs heterotypic gap junction communication. *Am J Physiol Cell Physiol* 282, C775-785 (2002).
31. Koike, N. et al. Tissue engineering: creation of long-lasting blood vessels. *Nature* 428, 138-139 (2004).
32. Koob, S. et al. Bone formation and neovascularization mediated by mesenchymal stem cells and endothelial cells in critical-sized calvarial defects. *Tissue Eng Part A* 17, 311-321 (2011)
33. Barberi T, et al. (2005) Derivation of Multipotent Mesenchymal Precursors from Human Embryonic Stem Cells. *PLoS medicine* 2(6): e161.
34. James D, et al. (2010) Expansion and maintenance of human embryonic stem cell-derived endothelial cells by TGFbeta inhibition is Id1 dependent. *Nat Biotechnology* 28(2):161-6.
35. de Peppo G M, et al. Osteogenic potential of human mesenchymal stem cells and human embryonic stem cell-derived mesodermal progenitors: a tissue engineering perspective. *Tissue engineering. Part A* 2010, 16(11): 3413-3426.
36. Olivier E N, et al. Differentiation of human embryonic stem cells into bipotent mesenchymal stem cells. *Stem Cells* 2006, 24:1914-1922.
37. Villa-Diaz L G, et al. Derivation of mesenchymal stem cells from human induced pluripotent stem cells cultured on synthetic substrates. *Stem cells* 2012, 30(6):1174-1181.
38. Levenberg S, et al. Endothelial cells derived from human embryonic stem cells. Proc Natl Acad Sci USA. 2002, 99(7):4391-6.
39. Wang Z Z, et al. Endothelial cells derived from human embryonic stem cells form durable blood vessels in vivo. *Nat Biotechnol* 2007, 25(3):317-8.
40. Rufaihah A J, et al. Human induced pluripotent stem cell-derived endothelial cells exhibit functional heterogeneity. *Am J Transl Res* 2013, 5 (1): 21-35.
41. de Peppo, et al. Engineering bone tissue substitutes from human induced pluripotent stem cells. *Proc Natl Acad Sci USA* 2013, 110(21):8680-5.

While the foregoing invention has been described in some detail for the purposes of clarity and understanding, it will be clear to one skilled in the art from a reading of this disclosure that various changes in form and detail can be made without departing from the scope of the invention. The present invention is also further described by the following claims.

What is claimed is:

1. A method of preparing a bone tissue graft, the method comprising:
    a) obtaining a digital model of a bone tissue portion to be produced, repaired, or replaced, wherein the bone tissue portion has a longitudinal axis extending along the length of the bone tissue portion, and partitioning the digital model transversally along the longitudinal axis to generate two or more model segments, each model segment having a discoidal geometry with uniform thickness;
    b) preparing two or more bone tissue graft segments, wherein each bone tissue graft segment has a size and shape corresponding to that of a model segment of (a), and wherein preparing the two or more bone tissue graft segments comprises:
        i) obtaining a scaffold, wherein the scaffold has a size and shape corresponding to a model segment;
        ii) obtaining a culture vessel comprising a graft chamber, wherein the graft chamber has a size and shape corresponding to the model segment so as to accommodate the scaffold of (i) and wherein the culture vessel is a direct perfusion bioreactor;
        iii) applying one or more populations of cells to the scaffold; and
        iv) culturing the cells on the scaffold within the graft chamber of the culture vessel for 3 to 5 weeks to form a bone tissue graft segment, wherein culture medium is perfused through the scaffold, and wherein the cells are induced pluripotent stem cell derived mesenchymal progenitor cells; and
    c) after preparing said two or more bone tissue graft segments, assembling the two or more bone tissue graft segments prepared in (b) to form a bone tissue graft, wherein the bone tissue graft has a size and shape corresponding to that of the bone tissue portion of (a), and wherein each bone tissue graft segment has a maximum thickness of about one centimeter or less.

2. The method of claim 1, wherein the bone tissue graft segment is vascularized.

3. The method of claim 1, wherein each bone tissue graft segment has a thickness of from about 0.3 millimeters to about 10 millimeters.

4. The method of claim 1, wherein the culture vessel is a direct perfusion bioreactor and the culturing is carried out under press-fit conditions.

5. The method of claim 1, wherein the graft chamber comprises a graft chamber insert.

6. The method of claim 1, wherein the scaffold is generated using computer assisted manufacturing, three-dimensional printing, casting, milling, laser cutting, rapid prototyping, or any combination thereof.

7. The method of claim 1, wherein the cells comprise bone-forming cells and/or cells capable of differentiating into bone-forming cells.

8. The method of claim 1, wherein the cells comprise blood vessel-forming cells and/or cells capable of differentiating into blood vessel-forming cells.

9. The method of claim 1, wherein the cells comprise endothelial progenitor cells.

10. The method of claim 1, wherein the assembling of (c) comprises using a biocompatible adhesive, stitches, sutures, staples, plates, pins, screws, or any combination thereof.

11. The method of claim 1, wherein the graft chamber comprises polydimethylsiloxane (PDMS).

* * * * *